(12) United States Patent
Müller et al.

(10) Patent No.: US 11,992,561 B2
(45) Date of Patent: May 28, 2024

(54) ORAL THIN FILM OF POLYVINYL ALCOHOL AND POLYVINYL ALCOHOL-POLYETHYLENE GLYCOL GRAFT COPOLYMER

(71) Applicant: LTS LOHMANN THERAPIE-SYSTEME AG, Andernach (DE)

(72) Inventors: Markus Müller, Troisdorf (DE); Mario Ficker, Bonn (DE); Michael Linn, Waldböckelheim (DE); Florian Hammes, Andernach (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 0 days.

(21) Appl. No.: 17/900,616

(22) Filed: Aug. 31, 2022

(65) Prior Publication Data
US 2023/0165805 A1    Jun. 1, 2023

Related U.S. Application Data

(63) Continuation of application No. 17/522,200, filed on Nov. 9, 2021, now abandoned.

(30) Foreign Application Priority Data

Nov. 9, 2020   (DE) .................. 10 2020 129 394.1
Aug. 11, 2021  (DE) .................. 10 2021 120 937.4

(51) Int. Cl.
*A61K 9/70*    (2006.01)
*A61K 9/00*    (2006.01)
*A61K 31/135*  (2006.01)
*A61K 47/10*   (2017.01)
*A61K 47/32*   (2006.01)

(52) U.S. Cl.
CPC ............ *A61K 9/7007* (2013.01); *A61K 9/006* (2013.01); *A61K 31/135* (2013.01); *A61K 47/10* (2013.01); *A61K 47/32* (2013.01)

(58) Field of Classification Search
None
See application file for complete search history.

(56) References Cited

U.S. PATENT DOCUMENTS

2020/0016092 A1 *  1/2020  Bernardo ............... A61K 47/38
2020/0138714 A1 *  5/2020  Müller .................... A61P 25/28

FOREIGN PATENT DOCUMENTS

CA        3095979 A1      10/2019
CN      111447920 A        7/2020
DE     102017112527    * 12/2018

OTHER PUBLICATIONS

Office Action for German Application No. 21206774.8, dated Jan. 26, 2023, 3 pages.
Office Action for Chinese Application No. 202111319730.4, dated Sep. 19, 2023, 19 pages.

* cited by examiner

*Primary Examiner* — Tigabu Kassa
(74) *Attorney, Agent, or Firm* — Lippes Mathias LLP

(57) ABSTRACT

Described is an oral thin film comprising at least one matrix layer, wherein the at least one matrix layer comprises at least one pharmaceutically active agent, at least one polyvinyl alcohol and at least one polyvinyl alcohol-polyethylene glycol graft copolymer, a method for producing same, and use thereof as a medicament.

15 Claims, 34 Drawing Sheets

FIGS. 2A-C
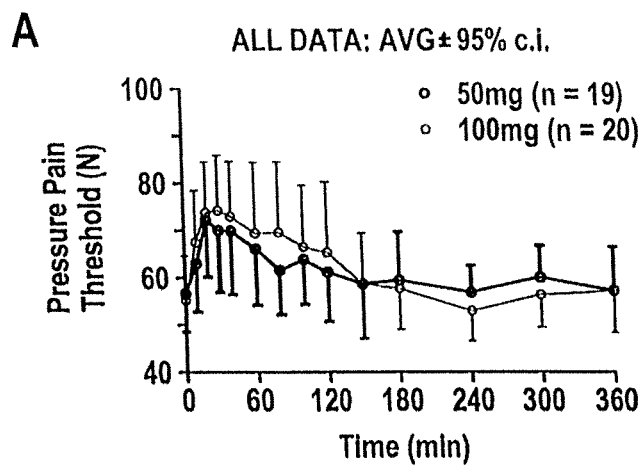
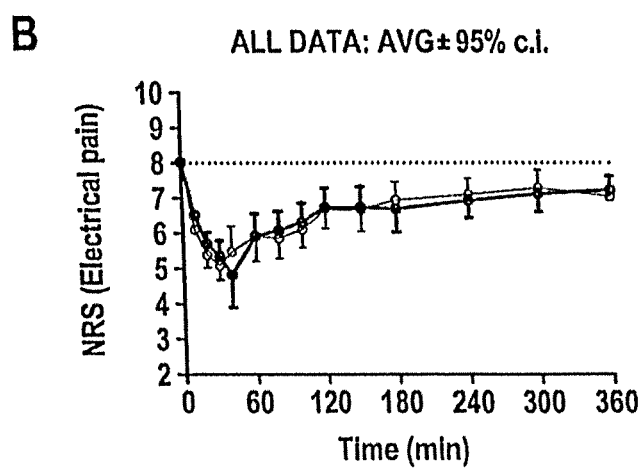
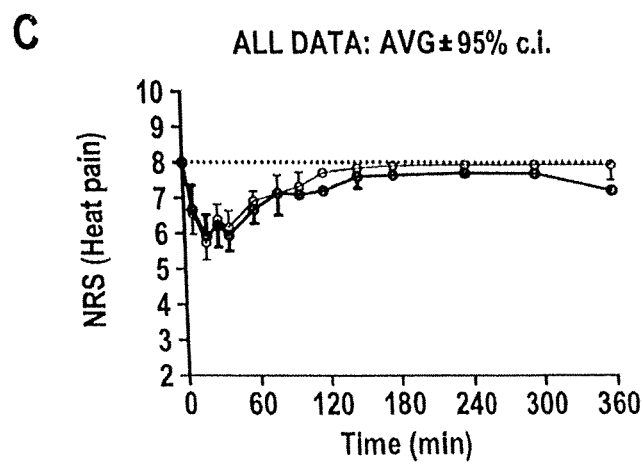

FIGS. 2D-F
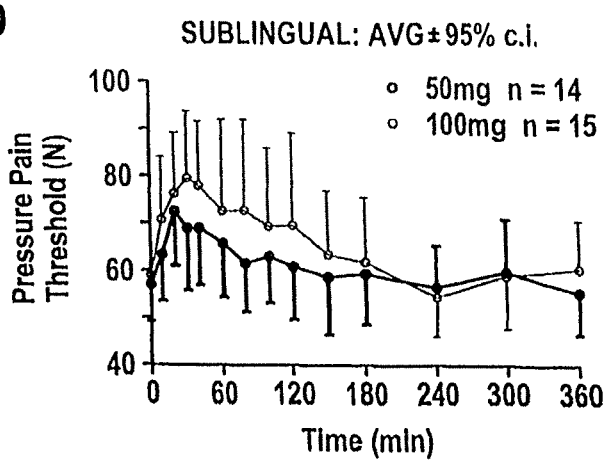
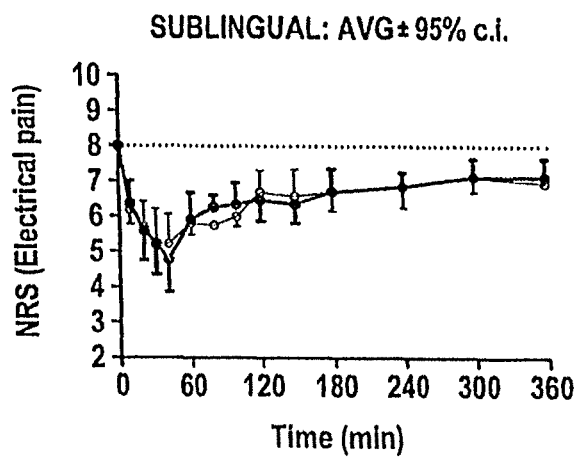
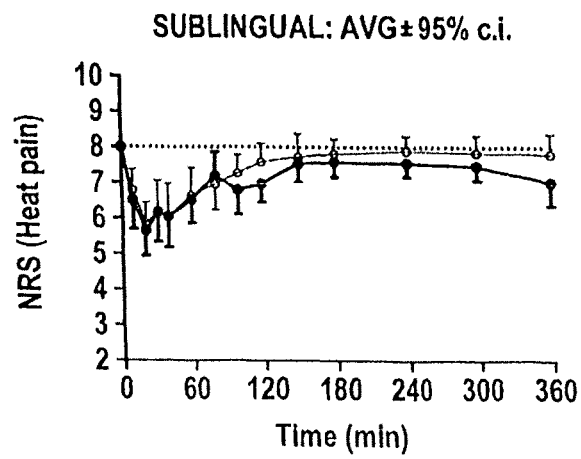

FIGS. 2G-I
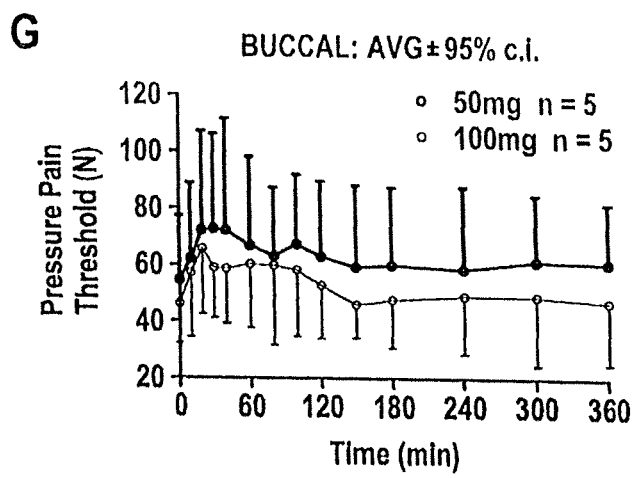
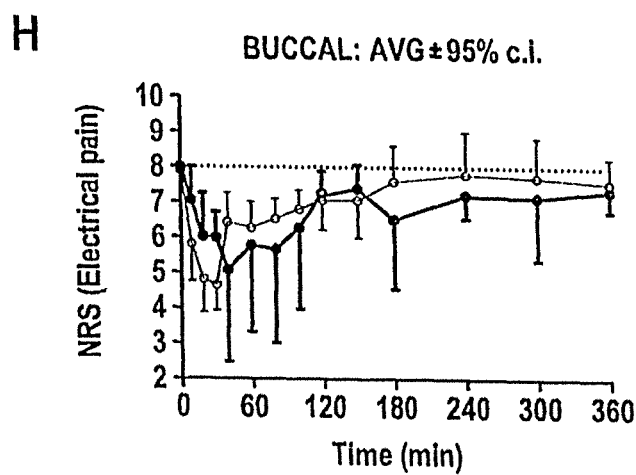
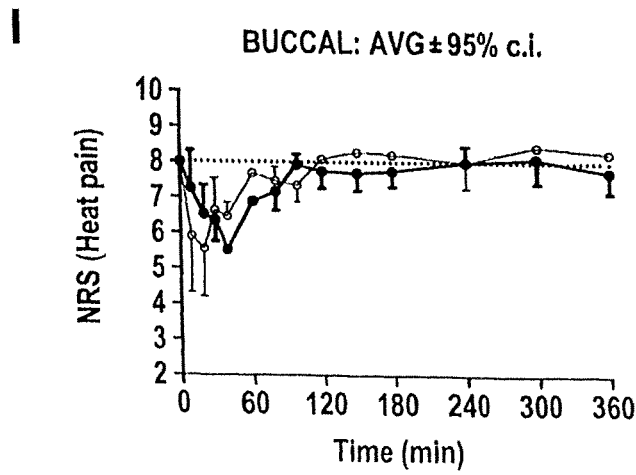

ORAL THIN FILM OF POLYVINYL ALCOHOL AND POLYVINYL ALCOHOL-POLYETHYLENE GLYCOL GRAFT COPOLYMER

This application is a continuation of U.S. Ser. No. 17/522,200, filed Nov. 9, 2021, the disclosure of which is herein incorporated by reference.

The present invention relates to an oral thin film containing at least one pharmaceutically active agent, a method for producing same, and the use of such an oral thin film as a medicament, especially in the treatment of pain and/or depression.

Oral thin films are thin films containing at least one pharmaceutically active agent that are placed directly in the oral cavity or against the oral mucosa and dissolve or macerate there and in so doing deliver the active agent. These films are, especially, thin active agent-containing polymer-based films which, when applied to a mucous membrane, especially the oral mucosa, can deliver the active agent directly into same. The very good blood supply to the oral mucosa ensures a rapid transfer of the active agent into the bloodstream. This dosage system has the advantage that the active agent is resorbed for the most part by the mucous membrane, thus avoiding the first-pass effect, which occurs in the case of the conventional dosage form of an active agent in tablet form. The active agent may be dissolved, emulsified or dispersed in the film.

As explained in greater detail further below, the oral thin film according to the invention preferably contains ketamine as pharmaceutically active agent and is preferably used for the treatment or prevention of pain.

The repositioning of ketamine from a medicinal perspective as an analgesic indicates the possibility of a new pain treatment option. Ketamine has proven to be effective in the treatment of moderate to severe pain and represents a useful alternative to opioid analgesia. Ketamine has also been found to reduce hyperalgesia (increased sensitivity to feeling pain), which occurs in many pain conditions, more specifically also by the long-term ingestion of opioids. In combination with opioids, ketamine also has the effect of reducing the dosage amount of opioids, which is necessary for achieving this analgesia.

The NMDA receptor antagonism of ketamine offers a "non-opioid" treatment option for the treatment of pain, which satisfies the unfulfilled requirements of the current therapy (for example reduced severe side effects in conjunction with opioids). (S)-ketamine, in comparison to the racemate, has approximately twice the analgesic effect as well as an anti-depressive effect. In contrast to opioids, the lethal dose of (S)-ketamine is very high (lethal dose averaged at 4.2 g/70 kg, for example lethal dose of fentanyl 2 mg/70 kg, oxycodone 40 mg/70 kg).

When administering some pharmaceutically active agents, high active agent loads of the oral thin film are desirable. A high active agent load in oral thin films is a known problem, since this can lead to brittle films or can directly prevent a film formation of the contained polymers. In order to achieve this nevertheless, large oral thin films or oral thin films with very high layer thicknesses are generally required. Large or thick oral thin films have the disadvantage that they cause problems with the application and may cause the patient to experience a sensation of a foreign body and may lead to long dissolving times.

Depending on the application, however, long disintegration times are undesirable.

In addition, known oral thin films with high active agent load have the disadvantage that the maximum area density and thus the amount of contained pharmaceutically active agent is determined by the drying of the oral thin film during production thereof. The greater is the area density of the oral thin film, the more pharmaceutically active agent may be contained therein, however, the drying time of the oral thin film is extended, as a result, to a time that is no longer economical, and in addition the active agent may be distributed inhomogeneously in the oral thin film.

BRIEF DESCRIPTION

The aim of the present invention lies in overcoming the above-mentioned disadvantages of the prior art. Especially, the aim of the present invention lies in providing an oral thin film for administering a high amount of at least one pharmaceutically active agent, wherein the oral thin film has an acceptable disintegration time, and wherein the pharmaceutically active agent is distributed relatively homogeneously in the oral thin film. Furthermore, the oral thin film will have a preferably pleasant and soft texture and therefore preferably will not trigger a sensation of a foreign body for the patient. The oral thin film according to the invention will also allow the greatest possible bioavailability of, for example, more than 10% or more than 20% or more than 30% or more than 40% or more than 50% or more than 60% or more than 70% or more than 80% or more than 90% of the pharmaceutically active agent.

The oral thin film according to the invention preferably has a bioavailability of 20 to 30% of the pharmaceutically active agent.

In addition, the oral thin film according to the invention will be designed such that approximately 40 to 60% of the contained pharmaceutically active agent can be released within the first minute following application, or approximately 75 to 90% of the contained pharmaceutically active agent can be released after the first two minutes following application.

In addition, once the oral thin film has been administered, minimal side effects will occur, especially minimal psychedelic effects (psychological and psychomimetic side effects).

In addition, it will be possible to produce the oral thin film as easily and economically as possible.

Especially, the at least one pharmaceutically active agent will comprise ketamine.

The above aim is addressed by an oral thin film according to claim 1, which has at least one matrix layer, wherein the at least one matrix layer comprises at least one pharmaceutically active agent, especially ketamine, at least one polyvinyl alcohol, and at least one polyvinyl alcohol-polyethylene glycol graft copolymer.

BRIEF DESCRIPTION OF THE DRAWINGS

FIGS. 2A-I are graphical depictions showing a reduction in pressure, electrical and heat pain;

DETAILED DESCRIPTION

Figure 1:
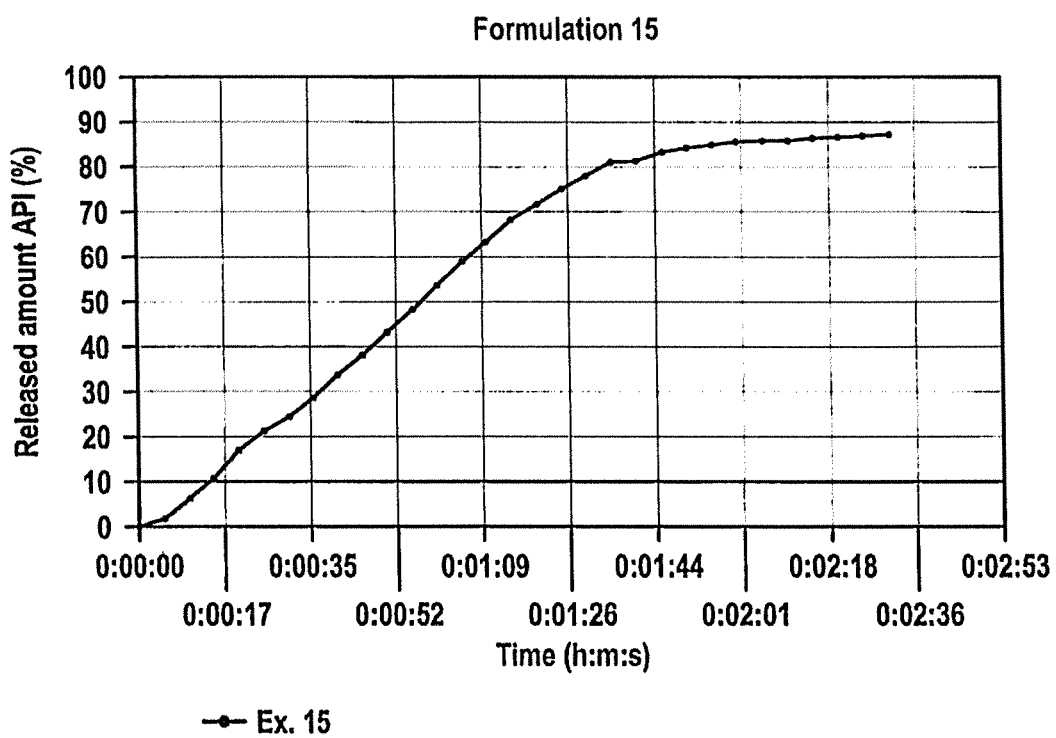
FIG. 1 is a graphical depiction of the results of a release study for Formulation 15.

It has been found that a polyvinyl alcohol-polyethylene glycol graft copolymer can absorb a high amount of active agent.

This has also been observed already in polyvinyl alcohols, where this effect is even more pronounced in part. Films based on polyvinyl alcohol alone, however, are hard and thus have a texture that is unpleasant for the patient.

Films based on a polyvinyl alcohol-polyethylene glycol graft copolymer alone, by contrast, have a softer texture since the polymer itself forms softer films. These films, however, are not quite so stable.

Due to the mixture of a polyvinyl alcohol-polyethylene glycol graft copolymer and a polyvinyl alcohol, it has been possible to achieve a film which, with a high active agent load, has the soft texture of a polyvinyl alcohol-polyethylene glycol graft copolymer film alongside a stability approaching that of a polyvinyl alcohol film.

The polyvinyl alcohol-polyethylene glycol graft copolymer preferably forms the basic structure and decisively determines the film properties, and the polyvinyl alcohol acts as an additional stabiliser.

A high active agent load with layer thicknesses and film sizes in acceptable ranges can thus be achieved. The dissolving times also lie in an acceptable range, the acceptable range preferably comprising values of less than 1 min. In addition, such an oral thin film is agreeable to the patient and can be produced easily and economically.

Preferred embodiments are described in the dependent claims.

In the present document, the word "comprising" can also mean "consisting of".

The oral thin film according to the invention has at least one matrix layer, wherein the at least one matrix layer comprises at least one pharmaceutically active agent, especially ketamine, at least one polyvinyl alcohol, and at least one polyvinyl alcohol-polyethylene glycol graft copolymer.

The at least one pharmaceutically active agent is not subject in principle to any limitation, but is preferably selected from all pharmaceutically active agents that are suitable for oral and/or transmucosal application.

According to the present invention, all pharmaceutically acceptable salts and solvates of the particular pharmaceutically active agent are also subsumed under the pharmaceutically active agent.

Active agents are preferably selected from the group comprising the active agent classes of analgesics, hormones, hypnotics, sedatives, antiepiletics, analeptics, psychoneurotropic drugs, neuro-muscle blockers, antspasmodics, antihistamines, antiallergics, cardiotonics, antiarrhythmics, diuretics, hypotensives, vasopressors, antidepressants, antitussives, expectorants, thyroid hormones, sexual hormones, antidiabetics, antitumour active agents, antibiotics, chemotherapeutics and narcotics, however, this group is not conclusive.

Polyvinyl alcohols (abbreviated to PVA or PVAL, sometimes also PVOH) are polymers of the general structure

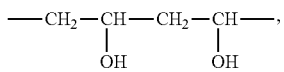

which can also contain small amounts (approximately 2%) of structural units of the type

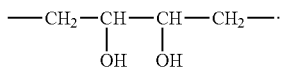

They belong to the group of vinyl polymers.

Commercially customary polyvinyl alcohols, which are offered in the form of white-yellow powder or granules, generally have a degree of hydrolysis of 98 to 99 or 87 to 89 mol %, that is to say also contain a residual content of acetyl groups. The polyvinyl alcohols are characterised by the manufacturer by a specification of the degree of polymerisation of the starting polymers or the mean molecular weight, the degree of hydrolysis, the saponification number or the solution viscosity.

Graft copolymers are branched polymers that contain different monomer units in the main chain and the branched chain.

The term "graft copolymers" is a common term.

The polyvinyl alcohol-polyethylene glycol graft copolymer provided here preferably has a main chain, comprising polyethylene glycol, onto which the polyvinyl alcohol units are grafted.

The oral thin film according to the invention is preferably also characterised in that the at least one pharmaceutically active agent comprises ketamine, preferably (S)-ketamine or a pharmaceutically acceptable salt thereof.

The oral thin film according to the invention in another embodiment is preferably characterised in that the at least one pharmaceutically active agent comprises ketamine, preferably R-ketamine or a pharmaceutically acceptable salt thereof.

Ketamine is preferably provided in the form of an HCl salt or in the form of a free base.

In the present case, ketamine is understood to mean (S)-(±)-2-(2-chlorophenyl)-2-(methylamino)cyclohexan-1-one, (R)-(±)-2-(2-chlorophenyl)-2-(methylamino)cyclohexan-1-one, and the racemate (RS)-(±)-2-(2-chlorophenyl)-2-(methylamino)cyclohexan-1-one.

After administration, ketamine is metabolised to norketamine, hydroxynorketamine and further substances.

Both (S)-ketamine and R-ketamine as well as a racemic mixture of these two can be contained in the matrix layer of the oral thin film according to the invention. However, (S)-ketamine in the form of a free base or a pharmaceutically acceptable salt thereof, especially (S)-ketamine HCl, is especially preferably present as a single stereoisomer of ketamine, since the analgesic and anaesthetic potency of (S)-ketamine is approximately three times higher than that of the (R) form.

The oral thin film according to the invention is also preferably characterised in that the at least one pharmaceutically active agent, preferably ketamine, is provided in the matrix layer in an amount of 45 to 70 wt. %, preferably of 50 to 65 wt. %, or of 55 to 65 wt. %, or of 55 to 60 wt. %, or of 60 to 65 wt. %, in relation to the total weight of the matrix layer.

Especially, the oral thin film according to the invention is preferably also characterised in that the at least one pharmaceutically active agent, preferably ketamine, is present in the matrix layer in an amount of 60 wt. %, in relation to the total weight of the matrix layer.

The oral thin film according to the invention is preferably also characterised in that the at least one pharmaceutically active agent, preferably ketamine, is present in the form of microcrystals.

Suitable mean crystal sizes of these microcrystals lie preferably in the range of 1 to 1000 µm or in the range of 5 to 500 µm or in the range of 10 to 200 µm. The mean crystal size especially preferably lies in the range of 15 to 25 µm, especially in the range of 20 to 22 µm. The crystal size can be determined, for example, by means of light microscopy or by means of micro computer tomography X-ray (micro-CT).

Unless stated otherwise, all cited molecular weights of polymers relate to the weight-average molecular weight (Mw), determined by means of gel permeation chromatography.

The oral thin film according to the invention is also preferably characterised in that the at least one polyvinyl alcohol comprises a polyvinyl alcohol with a mean molecular weight of approximately 25,000 to approximately 250,000 g/mol.

The oral thin film according to the invention is also preferably characterised in that the at least one polyvinyl alcohol comprises a polyvinyl alcohol with a mean molecular weight of approximately 25,000 to approximately 35,000 g/mol and/or a polyvinyl alcohol with a mean molecular weight of approximately 200,000 to 210,000 g/mol.

According to the present invention, polyvinyl alcohols with a mean molecular weight of approximately 31,000 (4-88) to approximately 205,000 (40-88) g/mol are especially suitable.

According to the present invention, polyvinyl alcohols with a mean molecular weight with approximately 31,000 (4-88) to approximately 205,000 (40-88) g/mol are especially suitable.

According to the present invention, polyvinyl alcohols with a viscosity of 3.4 to 4.6 mPas (4-88) to 34 to 46 mPas (40-88) mPas in a 40 g/l aqueous solution, determined by the "falling ball method" (Ph. Eur. 2.2.49), are also especially suitable, or mixtures of two or more different ones of these PVA types.

According to the present invention, polyvinyl alcohols with a viscosity of 3.4 to 4.6 mPas (4-88) or of 34 to 46 mPas (40-88) mPas in a 40 g/l aqueous solution, determined by the "falling ball method" (Ph. Eur. 2.2.49), are also especially suitable, or mixtures of two or more different ones of these PVA types.

The oral thin film according to the invention is also preferably characterised in that the at least one polyvinyl alcohol-polyethylene glycol graft copolymer has a polyethylene glycol main chain onto which there are grafted polyvinyl alcohol units.

The oral thin film according to the invention is also preferably characterised in that the at least one polyvinyl alcohol-polyethylene glycol graft copolymer has a polyethylene glycol main chain onto which there are grafted polyvinyl alcohol units, wherein the molar ratio of polyethylene glycol to polyvinyl alcohol is 1:3.

The oral thin film according to the invention is also preferably characterised in that the at least one polyvinyl alcohol-polyethylene glycol graft copolymer has a polyethylene glycol main chain onto which there are grafted polyvinyl alcohol units, wherein the polyvinyl alcohol-polyethylene glycol graft copolymer has a mean molecular weight in the range of 40,000 to 50,000 g/mol, preferably of approximately 45,000 g/mol.

A suitable and preferred polyvinyl alcohol-polyethylene glycol graft copolymer is known by the trade name Kollicoat IR (BASF).

The oral thin film according to the invention is also preferably characterised in that the at least one polyvinyl alcohol is provided in the matrix layer in an amount of 5 to 40 wt. %, preferably of 5 to 20 wt. %, of 5 to 19 wt. %, of 5 to 18 wt. %, of 5 to 17 wt. %, of 5 to 16 wt. %, of 5 to 15 wt. %, of 5 to 14 wt. %, of 5 to 13 wt. %, of 5 to 12 wt. %, of 5 to 11 wt. % or of 5 to 10 wt. %, in relation to the total weight of the matrix layer.

The oral thin film according to the invention is also preferably characterised in that the at least one polyvinyl alcohol-polyethylene glycol graft copolymer is provided in the matrix layer in an amount of 15 to 45 wt. %, preferably of 17 to 40 wt. %, or 20 to 30 wt. %, in relation to the total weight of the matrix layer.

In another embodiment, the oral thin film according to the invention is also preferably characterised in that the at least one polyvinyl alcohol-polyethylene glycol graft copolymer is provided in the matrix layer in an amount of 10 to 30 wt. %, preferably of 15 to 25 wt. %, of 17.5 to 22.5 wt. % or of 19 to 21 wt. %, especially of approximately 19.5 to 20.5 wt. %, and especially preferably of approximately 20 wt. % or of 20.1 wt. %, in relation to the total weight of the matrix layer.

The oral thin film according to the invention is also preferably characterised in that the matrix layer also comprises at least one auxiliary substance selected from the group comprising colouring agents, flavourings, sweeteners, softeners, taste-masking agents, emulsifiers, enhancers, pH regulators, humectants, preservatives and/or antioxidants.

Each of these auxiliary substances is preferably contained in each case in an amount of 0.1 to 15 wt. %, preferably of 0.1 to 10 wt. %, or of 0.1 to 5 wt. %, in relation to the total weight of the matrix layer.

Sweeteners, such as saccharin Na and/or sucralose are preferably contained in the matrix layer in a total amount of 2 to 5 wt. %, especially approximately 3 wt. %, in relation to the total weight of the matrix layer.

Apart from sweeteners, flavourings are preferably contained in the matrix layer in a total amount of 2 to 5 wt. %, especially approximately 3 wt. %, in relation to the total weight of the matrix layer.

Colouring agents are preferably contained in the matrix layer in a total amount of 0.1 to 1 wt. %, especially approximately 0.4 wt. %, in relation to the total weight of the matrix layer.

The oral thin film according to the invention is not subjected to any limitations in respect of its structure.

The oral thin film according to the invention can thus be provided in the form of a single-layer oral thin film and thus can consist merely of the matrix layer as defined above.

In another embodiment, the oral thin film according to the invention can thus be provided in the form of a multi-layer oral thin film and thus can contain further layers in addition to the matrix layer as defined above.

This plurality of layers can be laminated directly on top of one another or can be connected to an adhesive layer arranged in between.

An adhesive layer is understood to mean a layer that can act as an adhesive, as defined in DIN EN 923:2016-03. A non-adhesive layer therefore cannot act as an adhesive as defined above.

Especially, water-soluble adhesive layers as described in DE 10 2014 127 452 A1 are suitable as adhesive layers, and the content of that document in this regard is hereby expressly incorporated fully in the present disclosure.

For example, buffer layers for setting a pH value or slowly dissolving or insoluble layers which protect the oral thin film against premature erosion can be provided as further layers.

Alternatively, further matrix layers can be provided, which contain other pharmaceutically active agents or flavourings or taste-masking agents.

In one embodiment the oral thin film according to the invention is characterised in that the matrix layer is in the form of a smooth film. This means that the matrix layer, for example, is not provided in the form of a foam.

A smooth film is preferably characterised in that a smooth film has a volume fraction of 0 to 5%, in relation to the total volume of the matrix layer, of bubbles or cavities. The cavities are filled here preferably with air or a gas, preferably with an inert gas, especially preferably with nitrogen, carbon dioxide, helium or a mixture of at least two of these gases. The diameter of the bubbles or cavities generally lies in the range of 0.01 to 350 μm. The diameter of the bubbles or cavities especially preferably lies in the range of 10 and 200 μm.

In another embodiment the oral thin film according to the invention is characterised in that the matrix layer is in the form of a solidified film having cavities.

Especially, the infiltration of water or saliva or other bodily fluids into the interior of the dosage form is facilitates by the cavities and the associated larger surface of the films, and therefore the dissolving of the dosage form and the active agent release are accelerated.

In the case of a quickly resorbing active agent, the transmucosal resorption can be improved additionally by the quick dissolution of the matrix layer.

On the other hand, the wall thickness of said cavities is preferably low, since these represent, for example, solidified bubbles, and so these cavities dissolve or break down quickly.

A further advantage of this embodiment lies in the fact that, due to the formulation as a foam, a quicker drying can be provided than for a comparable, non-foamed composition, in spite of the comparatively high area density.

The multi-layer oral thin film according to the invention is preferably characterised in that the cavities are isolated from one another and are preferably provided in the form of bubbles, wherein the cavities are filled with air or a gas, preferably with an inert gas, especially preferably with nitrogen, carbon dioxide, helium or a mixture of at least two of these gases.

According to another embodiment it is provided that the cavities are connected to one another preferably by forming a cohesive channel system penetrating the matrix.

Said cavities preferably have a volume fraction of 5 to 98%, preferably of 50 to 80%, in relation to the total volume of the matrix layer. In this way, the advantageous effect of accelerating the dissolving of the matrix layer is favourably influenced.

Furthermore, surface-active substances or surfactants can be added to the matrix layer for foam formation or to the obtained foam before or after the drying in order to improve the stability of the foam before or after the drying.

A further parameter that influences the properties of the dosage form according to the invention is the diameter of the cavities or bubbles. The bubbles or cavities are preferably produced with the aid of a foaming machine, with which the diameter of the bubbles can be set within a wide range, almost arbitrarily. The diameter of the bubbles or cavities can thus lie in the range of 0.01 to 350 μm. The diameter especially preferably lies in the range of 10 and 200 μm.

The oral thin film according to the invention preferably has an area of 0.5 $cm^2$ to 10 $cm^2$, especially preferably of 2 $cm^2$ to 8 $cm^2$ or of 4 $cm^2$ to 5 $cm^2$.

The area density of the matrix layer or of a further layer possibly provided is, in each case, preferably at least 10 $g/m^2$, more preferably at least 20 $g/m^2$ or at least 30 $g/m^2$ or most preferably 50 $g/m^2$, or less than or equal to 400 $g/m^2$, more preferably less than or equal to 350 $g/m^2$, or less than or equal to 300 $g/m^2$ or most preferably less than 250 $g/m^2$. The area density is preferably 10 to 400 $g/m^2$, more preferably 20 to 350 $g/m^2$, or 30 to 300 $g/m^2$ and most preferably 50 to 250 $g/m^2$.

Each of the provided layers, especially the matrix layer, preferably has in each case a layer thickness of preferably 10 μm to 500 μm, especially preferably of 20 μm to 300 μm.

If the various layers, especially the matrix layer, are present in the form of a solidified foam, it is thus preferred that each of the layers provided as a foam has, in each case, a layer thickness of preferably 10 μm to 3000 μm, especially preferably of 90 μm to 2000 μm.

The oral thin film according to the invention is also preferably characterised in that the at least one pharmaceutically active agent is present in the matrix layer in a total amount of 25 mg to 150 mg, preferably of 25 mg to 125 mg, especially of approximately 50 mg to 150 mg.

The oral thin film according to the invention is especially characterised in that the at least one pharmaceutically active agent is present in the matrix layer in a total amount of 50 mg to 100 mg, preferably of approximately 50 mg or approximately 100 mg.

The oral thin film according to the invention is also preferably characterised in that the at least one pharmaceutically active agent comprises ketamine, preferably in the form of a free base or ketamine HCl, in a total amount of 25 mg to 150 mg, preferably of 25 mg to 125 mg, especially of approximately 50 mg to 150 mg.

The oral thin film according to the invention is especially characterised in that the at least one pharmaceutically active agent ketamine, preferably in the form of a free base or ketamine HCl, is present in the matrix layer in a total amount of 50 mg to 100 mg, preferably of approximately 50 mg or approximately 100 mg.

The oral thin film according to the invention is also preferably characterised in that the at least one pharmaceutically active agent is present as ketamine, preferably in the form of a free base or ketamine HCl, is present in the matrix layer in a total amount of 25 mg to 150 mg, preferably of 25 mg to 125 mg, especially of approximately 50 mg to 150 mg.

The oral thin film according to the invention is especially characterised in that the at least one pharmaceutically active agent as ketamine, preferably in the form of a free base or ketamine HCl, is present in the matrix layer in a total amount of 50 mg to 100 mg, preferably of approximately 50 mg or approximately 100 mg.

The oral thin film according to the invention is also preferably characterised in that the at least one pharmaceutically active agent as ketamine, preferably in the form of a free base or ketamine HCl, is present in the matrix layer in a total amount of 2 mg or 5 mg or 7 mg or 10 mg or 15 mg or 20 mg or 25 mg or 30 mg or 35 mg or 40 mg or 45 mg or 50 mg or 55 mg or 60 mg or 65 mg or 70 mg or 80 mg or 90 mg or 95 mg or 100 mg or 105 mg or 110 mg or 115 mg or 120 mg or 125 mg or 130 mg or 135 mg or 140 mg or 145 mg or 150 mg.

The oral thin film according to the invention is also preferably characterised in that the puncture strength is at least 0.15 N/mm$^2$, preferably at least 0.18 N/mm$^2$, especially preferably 0.20 N/mm$^2$ or more. The area density here is preferably 150 to 250 g/m$^2$, especially preferably 180 to 220 g/m$^2$.

The puncture strength is preferably determined as follows:

Used test device: Sauter FH-20 force gauge.
Test area: round test area of diameter 5 mm.
Execution:

The force gauge is fixed and a 10 cm$^2$ laminate specimen is placed centrally on the test area of the device (round test area of diameter 5 mm). The laminate specimen is fixed at the edges and a force is exerted in the direction of the test specimen, which force is increased until the laminate specimen is punctured. The resultant maximum value of the force that was applied to the specimen until puncture is measured. The measurement is performed with n=3 laminate specimens per laminate batch.

The oral thin film according to the invention is also preferably characterised in that the bioavailability of the at least one pharmaceutically active agent, especially the ketamine, preferably in the form of a free base or ketamine HCl, is at least 5% or at least 10% or at least 15% or at least 20% or at least 25% or at least 30% or at least 35% or at least 40% or at least 45% or at least 50% or at least 55% or at least 60% or at least 65% or at least 70% or at least 75% or at least 80% or at least 85% or at least 90% or at least 95% or at least 97% or at least 99%

The oral thin film according to the invention is also preferably characterised by the following release rates, wherein the release rate relates to the release of the at least one pharmaceutically active agent, preferably the ketamine, after a certain time following application of the oral thin film according to the invention.

It is preferred if, after 1 min, at least 40% or at least 50% of the at least one pharmaceutically active agent, preferably the ketamine, are released.

It is preferred if, after 2 min, at least 75% or at least 80% or at least 85% of the at least one pharmaceutically active agent, preferably the ketamine, are released.

It is preferred if, after 15 s, approximately 5 to 10% of the at least one pharmaceutically active agent, preferably the ketamine, are released.

It is preferred if, after 30 s, approximately 20 to 25% of the at least one pharmaceutically active agent, preferably the ketamine, are released.

It is preferred if, after 45 s, approximately 30 to 40% of the at least one pharmaceutically active agent, preferably the ketamine, are released.

It is preferred if, after 1 min, approximately 50 to 60% of the at least one pharmaceutically active agent, preferably the ketamine, are released.

It is preferred if, after 1 min and 15 s, approximately 60 to 70% of the at least one pharmaceutically active agent, preferably the ketamine, are released.

It is preferred if, after 1 min and 30 s, approximately 70 to 80% of the at least one pharmaceutically active agent, preferably the ketamine, are released.

It is preferred if, after 1 min and 45 s, approximately 80 to 85% of the at least one pharmaceutically active agent, preferably the ketamine, are released.

It is preferred if, after 2 min, approximately 82 to 88% of the at least one pharmaceutically active agent, preferably the ketamine, are released.

It is preferred if, after 2 min and 15 s, approximately 84 to 90% of the at least one pharmaceutically active agent, preferably the ketamine, are released.

It is preferred if, after 2 min and 30 s, approximately 86 to 92% of the at least one pharmaceutically active agent, preferably the ketamine, are released.

Hereinafter, preferred embodiments in respect of the maximum plasma concentration (Cmax) of the active agent or metabolites thereof will be described for the oral thin film according to the invention, in which (S)-ketamine is used as pharmaceutically active agent.

100 mg (S)-ketamine can be administered here in one dose or by means of two doses of 50 mg each of (S)-ketamine.

The oral thin film according to the invention is preferably characterised in that the maximum plasma concentration of (S)-ketamine following administration of a dose of 50 mg of (S)-ketamine lies at 50 to 200 ng/mL.

The oral thin film according to the invention is also preferably characterised in that the maximum plasma concentration of the ketamine metabolite (S)-norketamine following administration of a dose of 50 mg of (S)-ketamine lies at 200 to 400 ng/mL.

The oral thin film according to the invention is also preferably characterised in that the maximum plasma concentration of the ketamine metabolite (S)-hydroxynorketamine following administration of a dose of 50 mg of (S)-ketamine lies at 50 to 150 ng/mL.

The oral thin film according to the invention is preferably characterised in that the maximum plasma concentration of (S)-ketamine following administration of a dose of 100 mg of (S)-ketamine lies at 100 to 200 ng/mL.

The oral thin film according to the invention is also preferably characterised in that the maximum plasma concentration of the ketamine metabolite (S)-norketamine following administration of a dose of 100 mg of (S)-ketamine lies at 300 to 500 ng/mL.

The oral thin film according to the invention is also preferably characterised in that the maximum plasma concentration of the ketamine metabolite (S)-hydroxynorketamine following administration of a dose of 100 mg of (S)-ketamine lies at 100 to 250 ng/mL.

The oral thin film according to the invention is preferably characterised in that the maximum plasma concentration of (S)-ketamine following administration of a dose of 50 mg of (S)-ketamine lies at 70 to 120 ng/mL.

The oral thin film according to the invention is also preferably characterised in that the maximum plasma concentration of the ketamine metabolite (S)-norketamine following administration of a dose of 50 mg of (S)-ketamine lies at 200 to 300 ng/mL.

The oral thin film according to the invention is also preferably characterised in that the maximum plasma concentration of the ketamine metabolite (S)-hydroxynorketamine following administration of a dose of 50 mg of (S)-ketamine lies at 70 to 120 ng/mL.

The oral thin film according to the invention is preferably characterised in that the maximum plasma concentration of (S)-ketamine following administration of a dose of 100 mg of (S)-ketamine lies at 120 to 160 ng/mL.

The oral thin film according to the invention is preferably characterised in that the maximum plasma concentration of the ketamine metabolite (S)-norketamine following administration of a dose of 100 mg of (S)-ketamine lies at 300 to 350 ng/mL.

The oral thin film according to the invention is preferably characterised in that the maximum plasma concentration of the ketamine metabolite (S)-hydroxynorketamine following administration of a dose of 100 mg of (S)-ketamine lies at 150 to 220 ng/mL.

The oral thin film according to the invention is preferably characterised in that the maximum plasma concentration of (S)-ketamine following sublingual administration of a dose of 50 mg of (S)-ketamine lies at 70 to 120 ng/mL.

The oral thin film according to the invention is preferably characterised in that the maximum plasma concentration of the ketamine metabolite (S)-norketamine following sublingual administration of a dose of 50 mg of (S)-ketamine lies at 200 to 300 ng/mL.

The oral thin film according to the invention is preferably characterised in that the maximum plasma concentration of the ketamine metabolite (S)-hydroxynorketamine following administration of a dose of 50 mg of (S)-ketamine lies at 70 to 120 ng/mL.

The oral thin film according to the invention is preferably characterised in that the maximum plasma concentration of (S)-ketamine following sublingual administration of a dose of 100 mg of (S)-ketamine lies at 120 to 160 ng/mL.

The oral thin film according to the invention is preferably characterised in that the maximum plasma concentration of the ketamine metabolite (S)-norketamine following sublingual administration of a dose of 100 mg of (S) ketamine lies at 300 to 350 ng/mL.

The oral thin film according to the invention is preferably characterised in that the maximum plasma concentration of the ketamine metabolite (S)-hydroxynorketamine following sublingual administration of a dose of 100 mg of (S)-ketamine lies at 150 to 220 ng/mL.

The oral thin film according to the invention is preferably characterised in that the maximum plasma concentration of (S)-ketamine following buccal administration of a dose of 50 mg of (S)-ketamine lies at 80 to 160 ng/mL.

The oral thin film according to the invention is preferably characterised in that the maximum plasma concentration of the ketamine metabolite (S)-norketamine following buccal administration of a dose of 50 mg of (S)-ketamine lies at 200 to 280 ng/mL.

The oral thin film according to the invention is preferably characterised in that the maximum plasma concentration of the ketamine metabolite (S)-hydroxynorketamine following buccal administration of a dose of 50 mg of (S)-ketamine lies at 60 to 100 ng/mL.

The oral thin film according to the invention is preferably characterised in that the maximum plasma concentration of (S)-ketamine following buccal administration of a dose of 100 mg of (S)-ketamine lies at 120 to 200 ng/mL.

The oral thin film according to the invention is preferably characterised in that the maximum plasma concentration of the ketamine metabolite (S)-norketamine following buccal administration of a dose of 100 mg of (S)-ketamine lies at 400 to 500 ng/mL.

The oral thin film according to the invention is preferably characterised in that the maximum plasma concentration of the ketamine metabolite (S)-hydroxynorketamine following buccal administration of a dose of 50 mg of (S)-ketamine lies at 120 to 200 ng/mL.

The oral thin film according to the invention is also preferably characterised in that the matrix layer comprises 60 wt. % of (S)-ketamine HCl, 10 wt. % of the polyvinyl alcohol 40-88 as defined previously, and 20 wt. % or 20.1 wt. % of a polyvinyl alcohol-polyethylene glycol graft copolymer as defined previously.

The oral thin film according to the invention is also preferably characterised in that the matrix layer comprises 60 wt. % of (S)-ketamine HCl, 10 wt. % of the polyvinyl alcohol 40-88 as defined previously, and 20.1 wt. % of a polyvinyl alcohol-polyethylene glycol graft copolymer, preferably as defined previously, 1.0 wt. % of saccharin Na, 2.0 wt. % of sucralose, 3.5 wt. % of glycerol, 3.0 wt. % of a pharmaceutically acceptable flavouring and 0.4 wt. % of a pharmaceutically acceptable colouring agent. Pure water is preferably used here as solvent.

In a very especially preferred embodiment the oral thin film has a formulation according to formulation 15 in Table 3.

The oral thin film according to the invention can be produced by conventional methods.

The above definitions in relation to the oral thin film apply similarly for the method according to the invention.

A method for producing the oral thin film according to the invention preferably comprises the steps of:
a) producing a solution, dispersion or melt comprising the at least one pharmaceutically active agent, the at least one polyvinyl alcohol and the at least one polyvinyl alcohol-polyethylene glycol graft copolymer;
a1) optionally foaming the solution, dispersion or melt from step a) by introducing a gas or gas mixture, by chemical gas generation or by expansion of a dissolved gas,
b) the solution, dispersion or melt from step a) or the optionally foamed solution, dispersion or melt from step a1.

It is clear to a person skilled in the art that step a1) is necessary only if the matrix layer is to be provided in the form of a solidified foam having cavities.

The bubbles or cavities are preferably produced with the aid of a foaming machine, with which the diameter of the bubbles can be set within a wide range, almost arbitrarily.

The present invention also relates to an oral thin film obtainable by the method described above.

In addition, the present invention relates to an oral thin film, as described above or obtainable by the above-described method, as a medicament.

In addition, the present invention relates to an oral thin film, as described above or obtainable by the above-described method, as a medicament for sublingual and/or buccal administration.

In addition, the present invention relates to an oral thin film, as described above or obtainable by the above-described method, as a medicament for use in the treatment of pain and/or depression.

In addition, the present invention relates to an oral thin film, as described above or obtainable by the above-described method, as a medicament for use in the treatment of pain and/or depression by sublingual and/or buccal administration of the oral thin film.

The present invention additionally relates to an oral thin film, as described above or obtainable by the above-described method, wherein ketamine, preferably (S)-ketamine, or a pharmaceutically acceptable salt thereof, is used as pharmaceutically active agent in the matrix layer, for use in the treatment of pain and/or depression, especially to reduce the risk of suicide and/or for use as a general anaesthetic, preferably to initiate and carry out general anaesthesia, or as a supplement in the case of local anaesthesia and/or as an analgesic.

The present invention relates especially to an oral thin film as described above or obtainable by the above-described method, wherein ketamine, preferably (S)-ketamine, or a pharmaceutically acceptable salt thereof is used as pharmaceutically active agent in the matrix layer, for use in the treatment of pain, preferably as defined hereinafter.

The term "pain" is generally understood to mean a feeling of pain that is often caused by intense or noxious stimuli. Pain that is chronic or ongoing is understood to be long-lasting, and pain that disappears quickly is said to be acute.

Nociceptive pain is pain caused by the stimulation of sensory nerve fibres which respond to stimuli approaching or surpassing a noxious intensity (nociceptors) and can be classified according to the mode of the noxious stimulation. The most common categories are thermal, mechanical and chemical stimulation. Some nociceptors respond to more than one modality and are therefore termed as being polymodal.

Nociceptive pain can also be subdivided into "visceral", "deep somatic" and "superficial somatic" pain.

Neuropathic pain is generally caused by an injury or illness affecting a part of the nervous system involved in body sensation (the somatosensory system).

Neuropathic pain can be subdivided into peripheral, central or mixed (peripheral and central) neuropathic pain. Peripheral neuropathic pain is often described as "burning", "tingling", "electric" or "piercing".

The present invention also relates to a method for treating pain and/or depression in a patient, comprising the application of an oral thin film, as described above, to a mucous membrane of the patient.

The method for treating pain and/or depression in a patient is preferably characterised in that the mucous membrane comprises the oral mucosa.

The method for treating pain and/or depression in a patient is preferably characterised in that the oral thin film according to the invention is applied sublingually or buccally.

The method for treating pain and/or depression in a patient is preferably characterised in that the dosing of the at least one pharmaceutically active agent, preferably ketamine, especially in the form of a free base or ketamine HCl, is approximately 50 mg to 150 mg, preferably approximately 50 mg or approximately 100 mg.

The method for treating pain and/or depression in a patient is preferably characterised in that the oral thin film preferably is applied for a period of less than 2 min, especially of 30 s to 90 s, preferably of 30 s to 60 s and preferably dissolves during this time.

The invention will be described in greater detail hereinafter on the basis of non-limiting examples.

EXAMPLES

Example 1

The starting materials stated in Table 1 were used in the following examples.

TABLE 1

| Starting material | Function |
| --- | --- |
| (S)-ketamine HCl | API |
| Polyvinyl alcohol (PVA) 4-88 (35% solution) | Matrix polymer |
| Polyvinyl alcohol (PVA) 40-88 (15% solution) | Matrix polymer |
| Kollicoat IR (30% solution) | Matrix polymer |
| Glycerol | Plasticiser |
| Sucralose | Sweetener |
| Saccharin Na | Sweetener |
| Cherry Flavour M55394 (EU taste) | Flavouring |
| FD&C Red 40 | Colouring agent |
| Purified water | Process solvent |
| P 120 g/m$^2$, PE2 AB1 | Coating liner |

A plurality of oral thin films were produced from these starting materials by the method according to the invention and were examined. The composition of these is stated in Table 2.

TABLE 2

| Material | 1 [wt. %] | 2 [wt. %] | 3 [wt. %] | 4 [wt. %] | 5 [wt. %] | 6 [wt. %] | 7 [wt. %] | 8 [wt. %] | 9 [wt. %] | 10 [wt. %] |
| --- | --- | --- | --- | --- | --- | --- | --- | --- | --- | --- |
| (S)-ketamine HCl | 55.0 | 50.0 | 50.0 | 60.0 | 60.0 | 55.0 | 60.0 | 65.0 | 60.0 | 60.0 |
| PVA 4-88 | 35.0 | — | — | 30.5 | — | — | — | — | — | — |
| PVA 40-88 | — | — | 9.9 | — | 7.6 | 8.8 | 9.9 | 6.4 | — | 2.0 |
| Kollicoat IR | — | 39.5 | 29.6 | — | 22.9 | 26.2 | 20.6 | 19.1 | 30.5 | 28.5 |
| Saccharin Na | 1.0 | 1.0 | 1.0 | 1.0 | 1.0 | 1.0 | 1.0 | 1.0 | 1.0 | 1.0 |
| Sucralose | 2.0 | 2.0 | 2.0 | 2.0 | 2.0 | 2.0 | 2.0 | 2.0 | 2.0 | 2.0 |
| Glycerol | 4.0 | 4.0 | 4.5 | 3.5 | 3.5 | 4.0 | 3.5 | 3.5 | 3.5 | 3.5 |
| Cherry Flavour M55394 | 3.0 | 3.0 | 3.0 | 3.0 | 3.0 | 3.0 | 3.0 | 3.0 | 3.0 | 3.0 |
| Solvent | Aq. Pur. | Aq. Pur. | Aq. Pur. | Aq. Pur. | Aq. Pur. | Aq. Pur. | Aq. Pur. | Aq. Pur. | Aq. Pur. | Aq. Pur. |
| Foam/Film | Foam | Film | Foam | Foam | Foam | Foam | Foam | Foam | Film | Foam |

All oral thin films according to the invention with the compositions stipulated in Table 2 solve the problem addressed by the invention.

Based on composition 2, further oral thin films were produced having the composition according to Table 3 and were tested.

TABLE 3

| Material | 11 [wt. %] | 12 [wt. %] | 13 [wt. %] | 14 [wt. %] | 15 [wt. %] |
|---|---|---|---|---|---|
| (S)-ketamine HCl | 60.0 | 55.0 | 60.0 | 60.0 | 60.0 |
| PVA 4-88 | — | — | 5.0 | 10.0 | — |
| PVA 40-88 | 5.0 | 5.0 | — | — | 10.0 |
| Kollicoat IR | 25.1 | 30.1 | 25.1 | 20.1 | 20.1 |
| Saccharin Na | 1.0 | 1.0 | 1.0 | 1.0 | 1.0 |
| Sucralose | 2.0 | 2.0 | 2.0 | 2.0 | 2.0 |
| Glycerol | 3.5 | 3.5 | 3.5 | 3.5 | 3.5 |
| Cherry Flavour M55394 | 3.0 | 3.0 | 3.0 | 3.0 | 3.0 |
| FD&C Red No, 40 | 0.4 | 0.4 | 0.4 | 0.4 | 0.4 |
| Solvent | Aq. Pur. | Aq. Pur. | Aq. Pur. | Aq. Pur. | Aq. Pur. |
| Test | Good film, small particles visible | Good film, bubbles visible, rough surface | Good film, bubbles visible, rough surface | Good film, small particles visible | Very good film, few bubbles, very good tear strength |

All oral thin films with the compositions stipulated in Table 3 solve the problem addressed by the invention.

Formulation 15 was examined in detail.

Formulation 15 is stable for 9 months at 25° C./60 r.h. %-40°/r.h. 75%.

The residual water content of formulation 15 was determined by means of Karl Fischer titration.

The residual water content of 6 samples was determined. The determined residual water content was 4.40 wt. %, 3.82 wt. %, 4.02 wt. %, 4.51 wt. %, 4.91 wt. % and 4.57 wt. %.

This residual water content is acceptable.

The disintegration time of formulation 15 in a 1 L glass beaker with 900 ml demineralised water (temperature-controlled to 37° C.±2° C.) was determined.

The disintegration time of six samples was determined. The determined disintegration time was 52 s, 55 s, 58 s, 56 s, 54 s and 55 s.

Formulation 15 thus has a good disintegration time.

The in vitro release of the active agent was also determined from formulation 15.

With the in vitro release, (S)-ketamine is released from (S)-ketamine HCl-containing oral thin films and is determined. The active agent is released in phosphate buffer pH 6.8 USP and is then determined by in situ fibre optic UV system. The quantification was performed against an external standard.

The release is performed with Dissolution Apparatus 2—(Paddle over sinker) according to USP <711>,

TABLE 4

| | |
|---|---|
| Sinker: | Stainless Steel Capsule Sinker with 10 Spirals, 31.0 × 11.0 mm Capacity (Sotax Style) |
| Stirring speed: | 50 rpm |
| Distance between the vessel base and the lower edge of the paddle: | 25 mm ± 2 mm |
| Temperature: | 37° C. ± 0.5° C. |
| Release medium: | Phosphate buffer pH 6.8 USP |
| Release medium volume: | 500 mL |
| Sample measurement intervals: | Every 5 seconds (0 to 5 min) Every 10 seconds (5 to 10 min) Every 15 seconds (10 to 15 min) |

The results of the release study are shown and FIG. 1 and were as follows:

| | |
|---|---|
| after 15 s | approx. 11% |
| after 30 s | approx. 24% |
| after 45 s | approx. 38% |
| after 1 minute | approx. 54% |
| after 1 minute 15 s | approx. 68% |
| after 1 minute 30 s | approx. 78% |
| after 1 minute 45 s | approx. 83% |
| after 2 minutes | approx. 85% |
| after 2 minutes 15 s | approx. 86% |
| after 2 minutes 30 s | approx. 87% |

Example 2

The formulations from Table 3 were examined in greater detail in further studies.

1. Measurement of the Puncture Strength

Execution of the measurement (test of the puncture strength of the laminate):

Used test device: Sauter FH-20 force gauge.

Test area: round test area of diameter 5 mm.

The commercially obtainable product: "LISTERINE POCKETPAKS® COOL MINT ORAL CARE FRESH BREATH STRIPS" was used as comparison product. This contains pullulan, menthol, Acesulfame potassium, copper gluconate, polysorbate 80, *Chondrus crispus* gum (Carrageenan), glyceryl oleate, thymol, eucalyptol, methyl salicylate, *Ceratonia siliqua* gum (locust bean gum), propylene glycol, xanthan gum, aroma (flavouring), FD&C Blue No. 1 (colouring agent) and FD&C Green No. 3 (colouring agent).

Execution:

The force gauge was fixed and a 10 cm² laminate specimen (for Listerine, a 32 mm×22 mm Listerine OTF was used) was placed centrally on the test area of the device (round test area of diameter 5 mm). The laminate specimen was fixed at the edges and a force was exerted in the direction of the test specimen; the force was increased until the laminate specimen was punctured. The resultant maximum value of the force that was applied to the test specimen until puncture was measured. The measurement was performed with n=3 laminate specimens per laminate batch (for Listerine, n=3 measurement with OTF).

The results are summarised in the following Table 5:

TABLE 5

| Formulation | Average [N] | Standard deviation [N] | Area density [g/m$^2$] | Puncture strength [N/mm$^2$] |
|---|---|---|---|---|
| 2 | 1.96 | 0.09 | 150 | 0.10 |
| 3 | 2.22 | 0.10 | 130 | 0.11 |
| 5 | 1.85 | 0.06 | 157 | 0.09 |
| 5 | 2.88 | 0.19 | 206 | 0.15 |
| 7 | 2.92 | 0.08 | 167 | 0.15 |
| 8 | 1.27 | 0.12 | 145 | 0.06 |
| 9 | 1.55 | 0.12 | 190 | 0.08 |
| 10 | 1.79 | 0.15 | 156 | 0.09 |
| 11 | 2.68 | 0.20 | 188 | 0.14 |
| 12 | 2.63 | 0.05 | 172 | 0.13 |
| 13 | 2.04 | 0.05 | 184 | 0.10 |
| 14 | 2.26 | 0.11 | 180 | 0.12 |
| 15 | 4.00 | 0.15 | 206 | 0.20 |
| Listerine (comparison) | 3.14 | 0.80 | 46.3 | 0.16 |

All shown examples have a good puncture strength (comparable to the product Listerine as reference) in spite of high active agent load.

Example 3

As stated in the description, the oral thin film according to the invention is preferably characterised in that the at least one pharmaceutically active agent, preferably ketamine, is present in the form of microcrystals. Suitable mean crystal sizes of these microcrystals lie preferably in the range of 1 to 1000 µm or in the range of 5 to 500 µm or in the range of 10 to 200 µm. The crystal size can be determined, for example, by means of light microscopy or by means of micro computer tomography X-ray (micro-CT).

Micro computer tomography (micro CT) x-ray test method and measurement conditions:
Instrument SkyScan 2211
X-ray energy 60 kV
Resolution 0.75 µm/voxel
Reconstruction according to Feldkamp The results are summarised in the following Table 6:

TABLE 6

| Formulation | Crystal size and standard deviation |
|---|---|
| 4 | 20.1 µm +− 7.2 µm |
| 7 | 18.4 µm +− 6.8 µm |
| 14 | 16.9 µm +− 6.2 µm |
| 15 | 21.0 µm +− 7.8 µm |

Example 4

Results of a clinical study with an OTF based on formulation 15 according to Table 3.
Aim:
Primary objective: Determination of the pharmacokinetic profile of an oral thin film of (S)-ketamine with 50 mg (S)-ketamine; Secondary objective: (1) Determination of the pharmacodynamic profile of an oral thin film of (S)-ketamine with 50 or 100 mg (S)-ketamine with the end points antinociceptors and psychomimetic side effects; (2) Determination of the safety and compatibility of the (S)-ketamine oral thin film.

Study Design:
The study had an explorative, open, crossover and randomised design. All test subjects were treated twice. The test subjects received 50 mg (S)-ketamine OTF once and two 50 mg (S)-ketamine OTF once (total dose thus 100 mg) in a random order. 15 test subjects received the OTF sublingually; 5 further test subjects received the OTF buccally.

Execution of the Study:
During one test run, the test subjects received an individual 50 mg (S)-ketamine OTF either sublingually (n=15) or buccally (n=5) During a further test run, the test subjects received simultaneously two 50 mg (S)-ketamine OTFs sublingually (n=15) or buccally (n=5) Six hours after the OTF administration, a low (S)-ketamine dose (20 mg) was administered to the test subjects intravenously. A wash-out phase of at least 2 days was provided between the study days.

Blood Sampling:
For blood sampling, an arterial access was placed in the left or right radial or brachial artery. Blood samples (4 ml) were taken at the following intervals following OTF administration (t=0 min): 0, 5, 10, 20, 40, 60, 90, 120, 180, 240, 300, 360 min and at the following intervals following the start of intravenous administration: 2, 4, 10, 15, 20, 30, 40, 60, 75, 90 and 120 min.

Pain Tests:
Three pain tests were performed at intervals of 10 to 20 minutes (at intervals of 10 to 60 minutes (0-10-20-30-40-60-80-100-120-150-180-240 360 minutes)
  a) pressure pain,
  b) electrical pain and
  c) heat-induced pain.
  a) The test subjects assessed their pressure pain threshold in response to an increasing pressure stimulus using an FDN 200 Algometer from Wagner Instruments.
  b) The test subject used a transcutaneous electrical pain model to assess the pain threshold during a fixed stimulation of the skin so that the pain value was 7 to 8.
  c) A fixed heat stimulus that caused a pain value of 7 to 8 was applied to the skin using the Medoc Pathway System.

All pain assessments were performed using an 11-stage Likert scale (Verbal Rating Scale, VRS), which ranged from 0 (no pain) to 10 (maximum pain imaginable).

Qualitative Results:
The taste of the film formulations was described by the test subjects as being acceptable. No safety-relevant results were reported. Neither the sublingual nor the buccal administration were considered to be problematic.

Plasma Concentrations:
The plasma concentration was measured by means of liquid chromatography coupled with QTOF-MS as detection method. The lower detection limit was 6 ng/mL, 6 ng/mL and 4 ng/mL for (S)-ketamine, (S)-norketamine and (S)-hydroxynorketamine respectively. The upper detection limit was 1000, 500 and 200 ng/mL for (S)-ketamine, (S)-norketamine and (S)-hydroxynorketamine respectively.

Questionnaires:
Immediately before the pain test, two questionnaires were filled out with an interval of 30 minutes in between in order to assess the effect of the medicinal treatment for psychological and psychomimetic side effects (0-30-60-90-etc. from 0 to 360 minutes).

1. Bowdle questionnaire: Based on the Bowdle questionnaire (Bowdle et al "Psychedelic effects of ketamine in healthy volunteers: relationship to steady-state plasma concentrations" Anesthesiology 1998 January; 88(1): 82-8) it is possible to deduce three factors of psychedelic effects: drug intoxication, internal perception and external perception.

2. Bond and Lader questionnaire: The Bond and Lader scales are calculated from sixteen 100 mm visual analogue scales. The end points are set to antonymous word pairs, such as 'awake-sleepy', 'well coordinated-clumsy', 'mentally slow-quickly attentive' and 'incompetent-professional'.

Results:

The results show the rapid onset of a powerful and long-lasting reduction in pain (see FIG. 2). No dose dependency for the pain relief was observed for the OTF formulation. This is presumably due to the high concentration of the metabolite norketamine, which brings about an anti-analgesic effect (see Olofsen et al "Estimation of contribution of norketamine to ketamine-induced acute pain relief and neurocognitive impairment in healthy volunteers" Anesthiology 2012; 117; Addendum 5).

A non-linear dose-dependent increase in the concentration of ketamine and the metabolites norketamine and hydroxynorketamine was observed for the OTF formulation.

Figure 3:
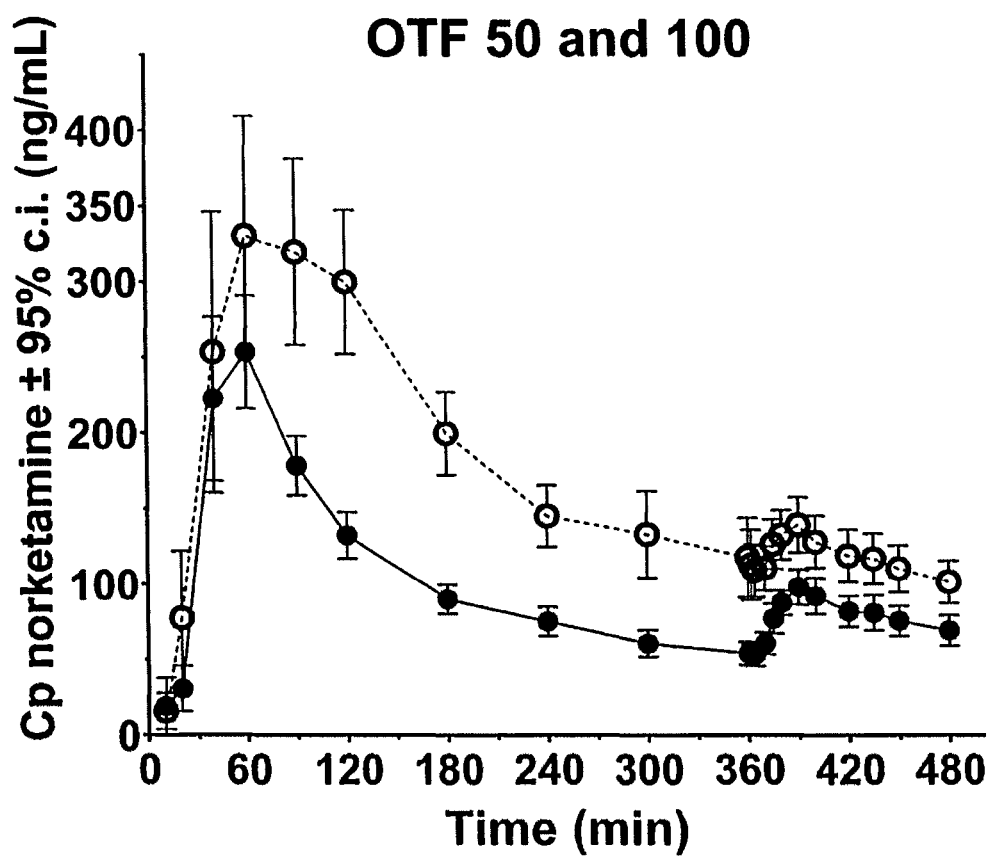
FIGS. 3-5 show the plasma level of the metabolite (S)-norketamine are higher following administration of an OTF as compared to intravenous-administration of 20 mg (S)-ketamine.
Figure 4:
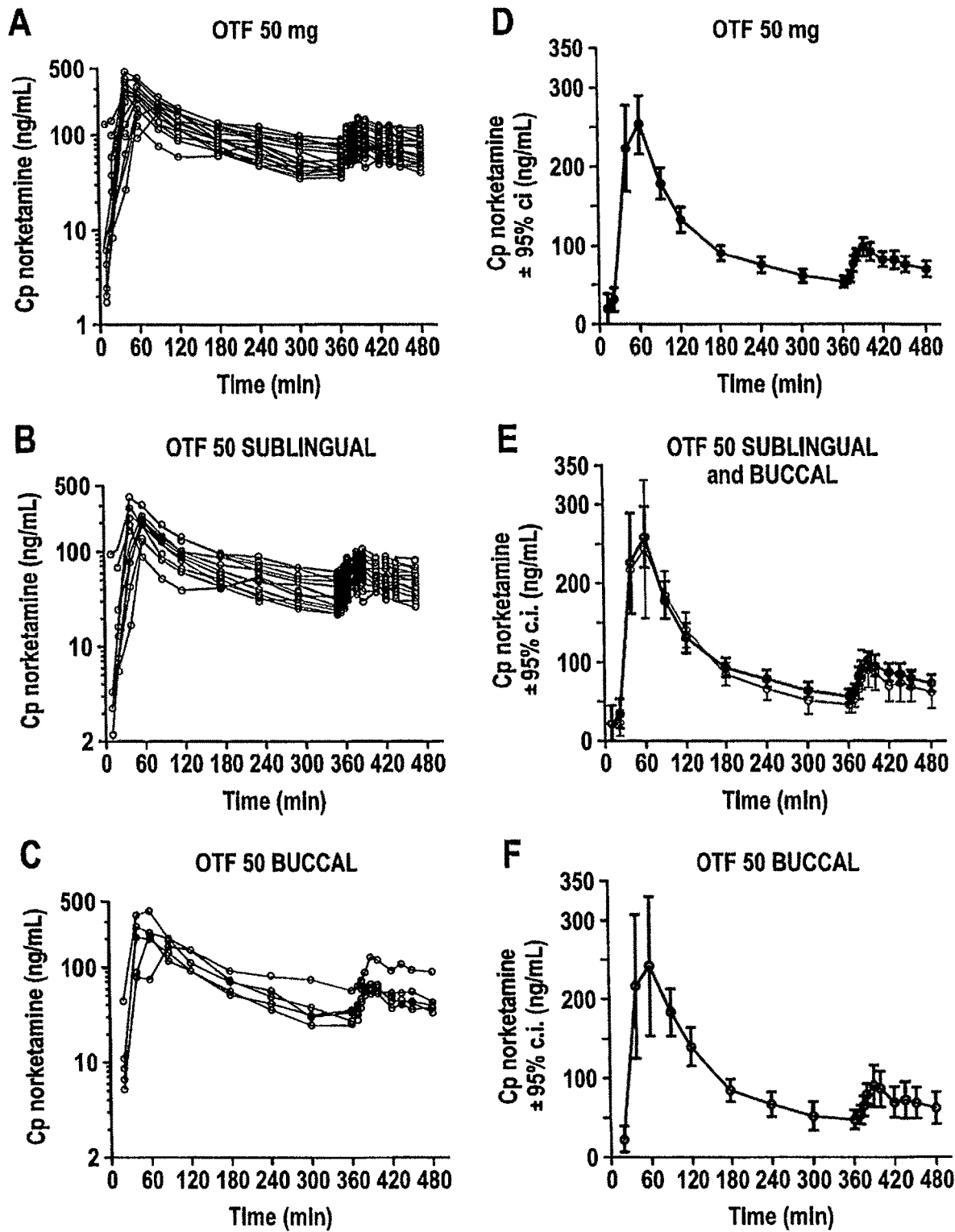
Figure 5:
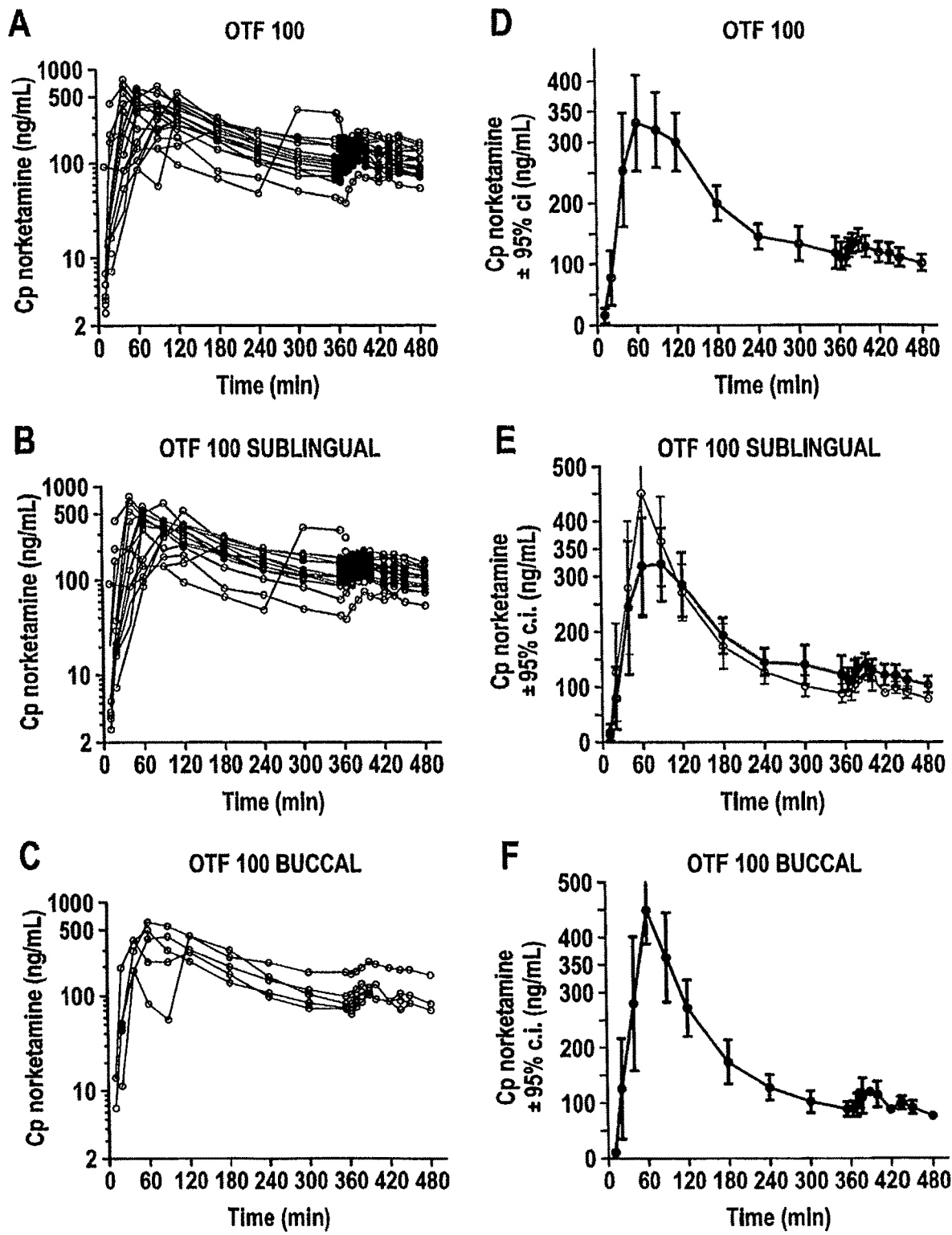
Figure 6:
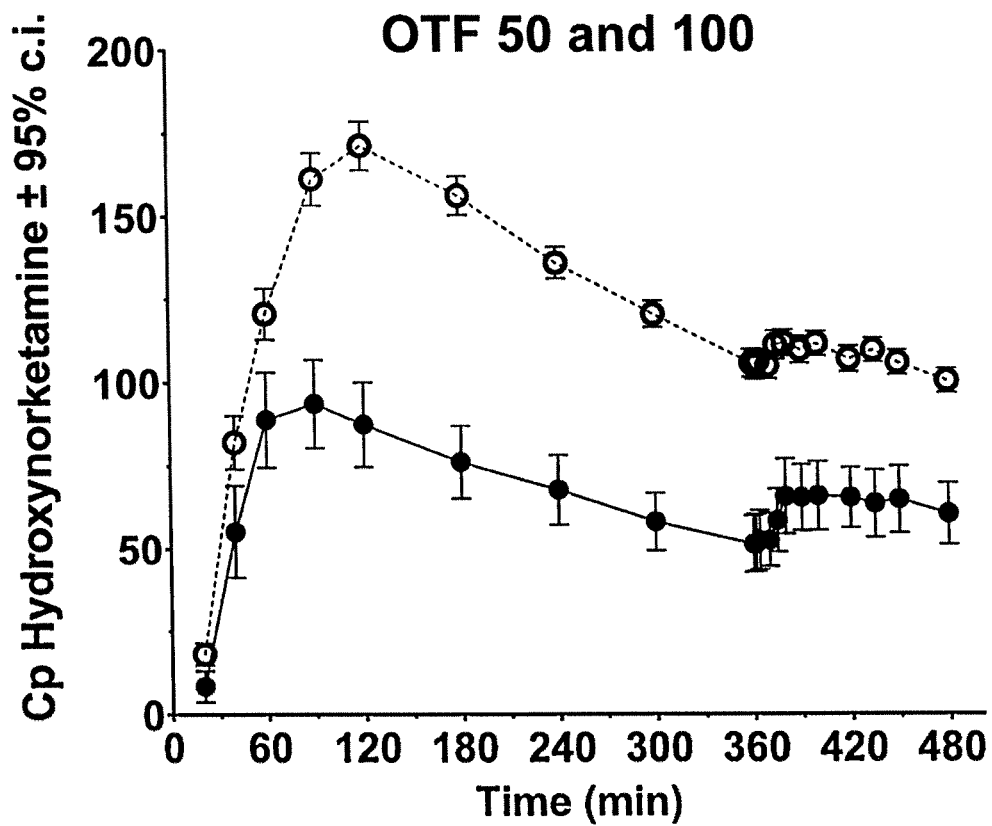
FIGS. 6-8 show the plasma level of the metabolite (S)-hydroxynorketamine are higher following administration of an OTF as compared to intravenous administration of 20 mg (S)-ketamine.
Figure 7:
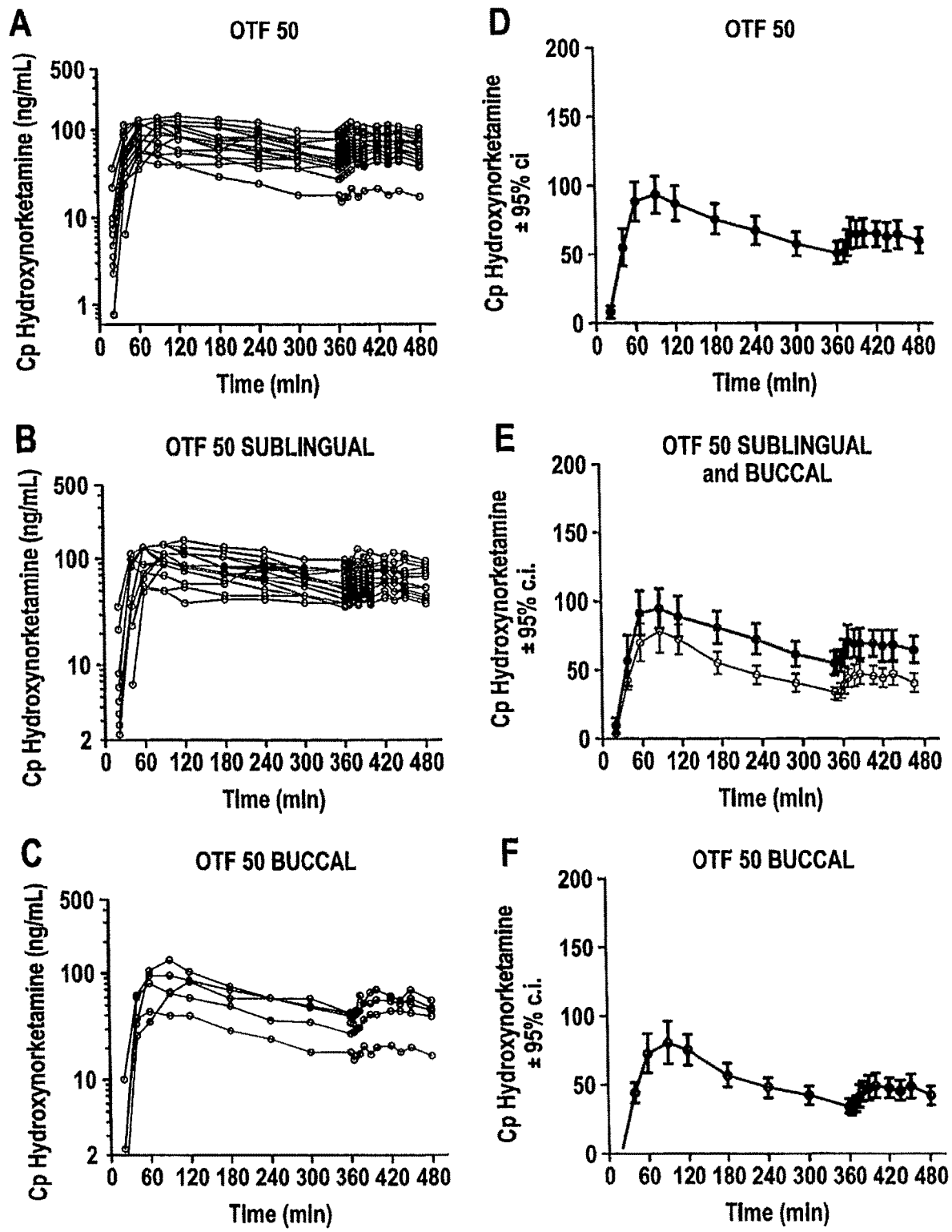
Figure 8:
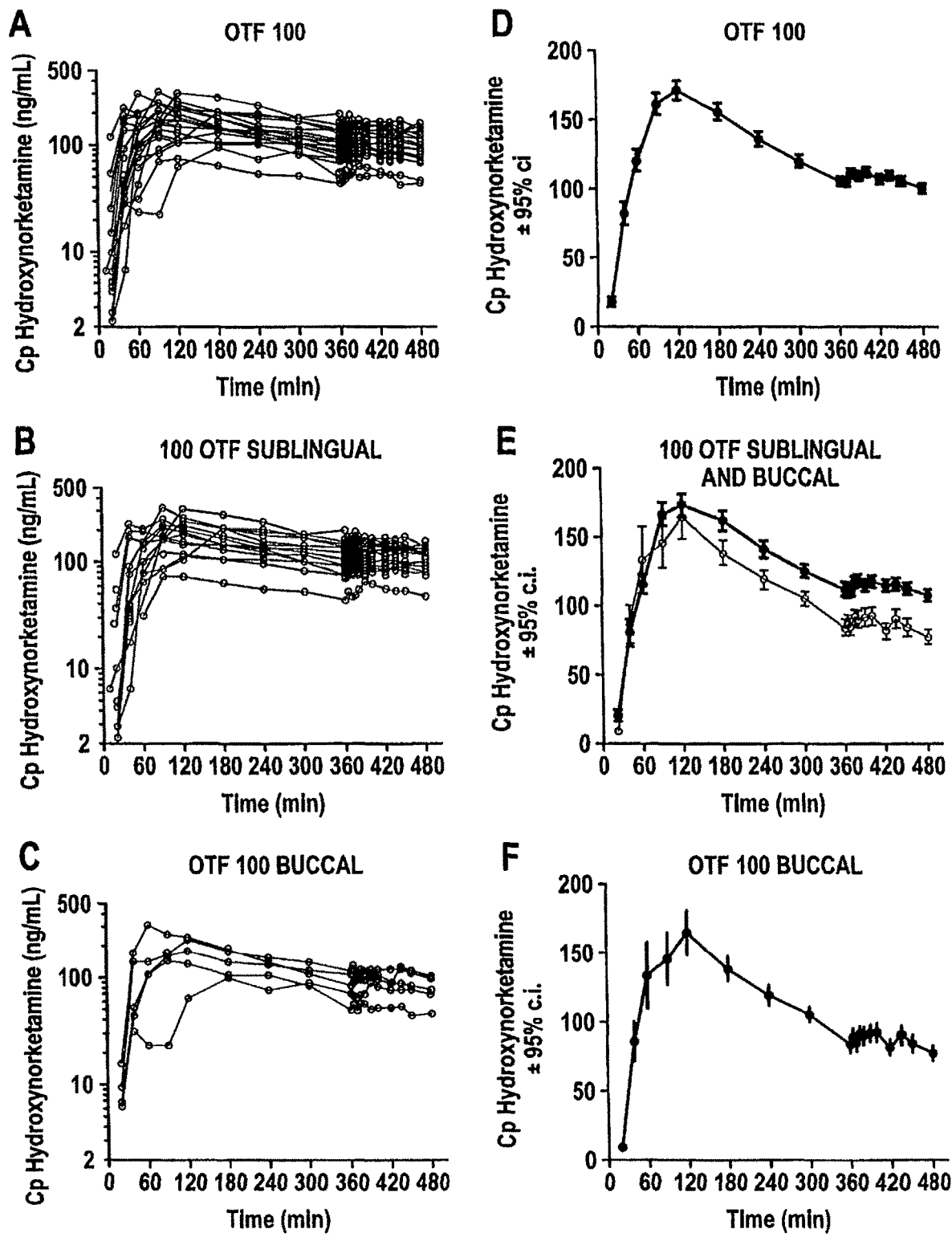

The plasma level of the metabolites (S)-norketamine (see FIGS. 3, 4 and 5) and (S)-hydroxynorketamine (FIGS. 6, 7 and 8) are higher following administration of an OTF (see also Table 7 below) as compared to intravenous administration of 20 mg (S)-ketamine.

Figure 9:
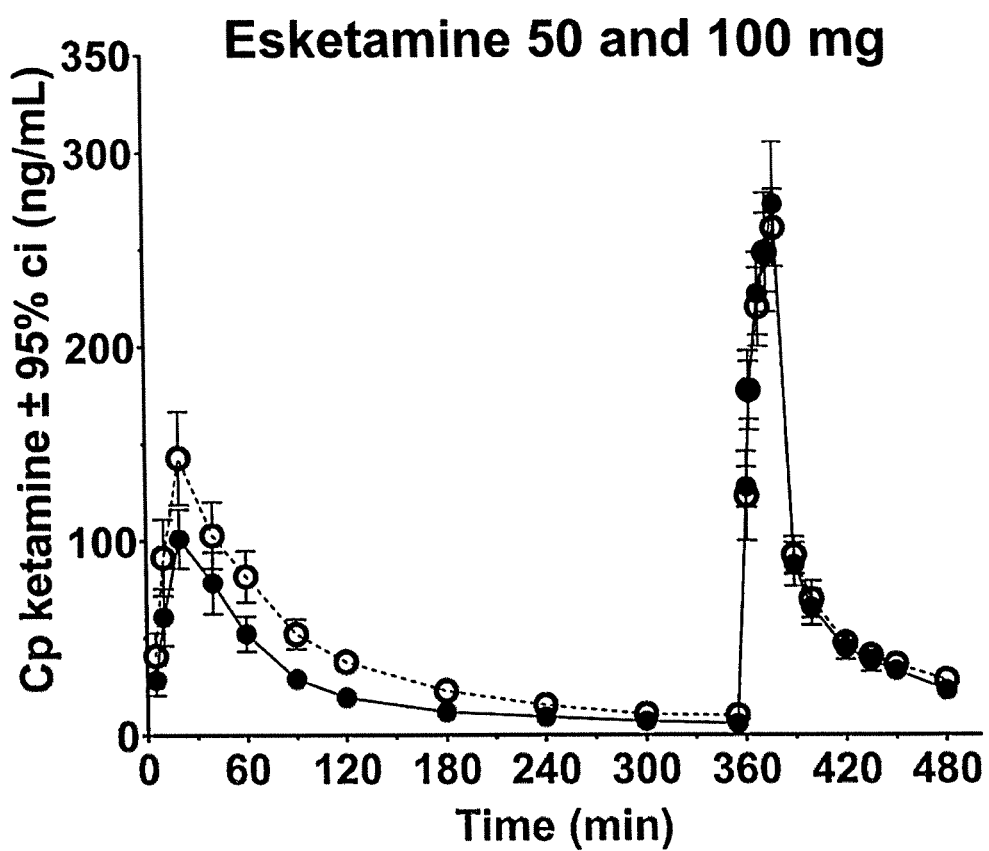
FIGS. 9-11 show the plasma levels of ketamine are higher for intravenous administration than following administration of an OTF.
Figure 10:
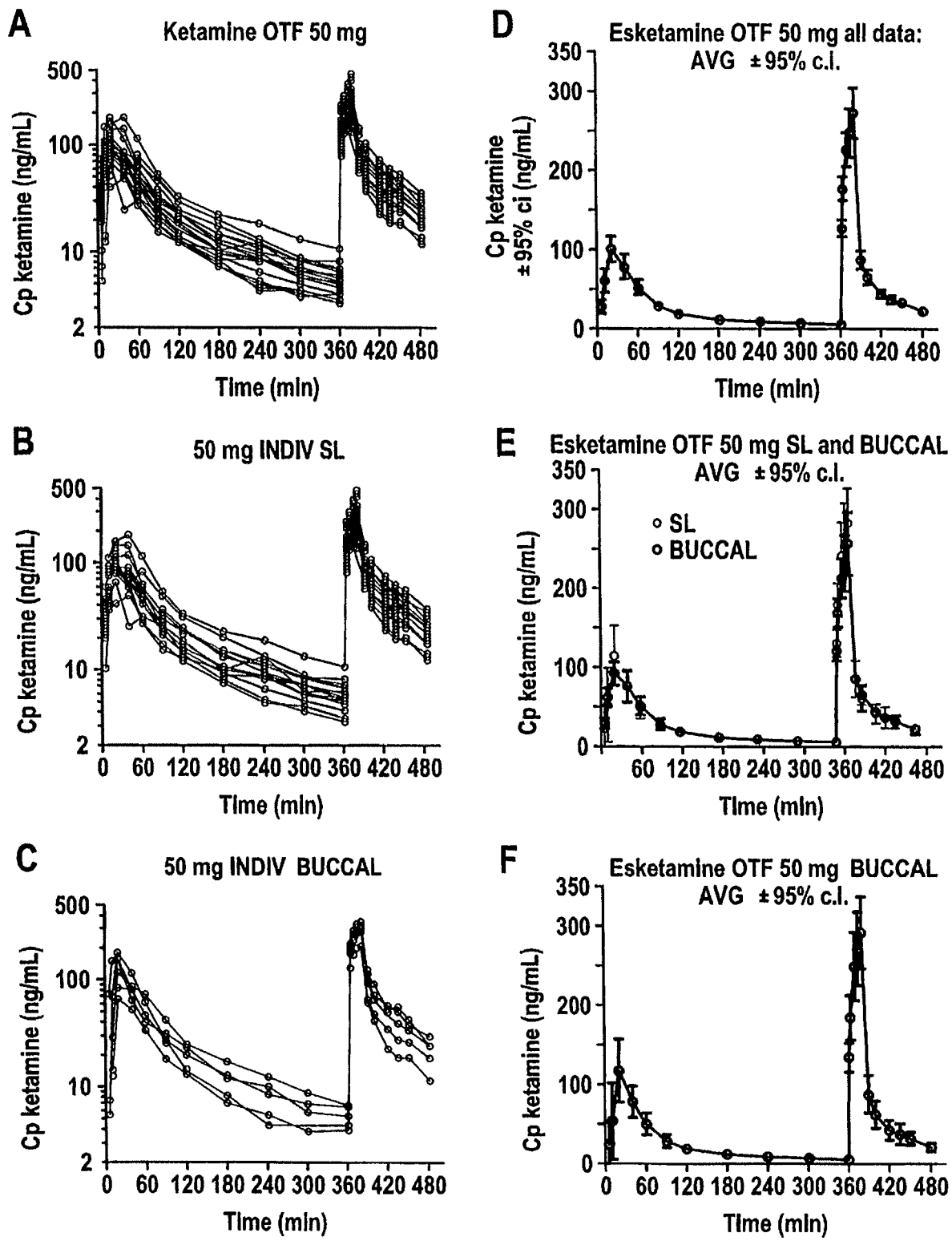
Figure 11:
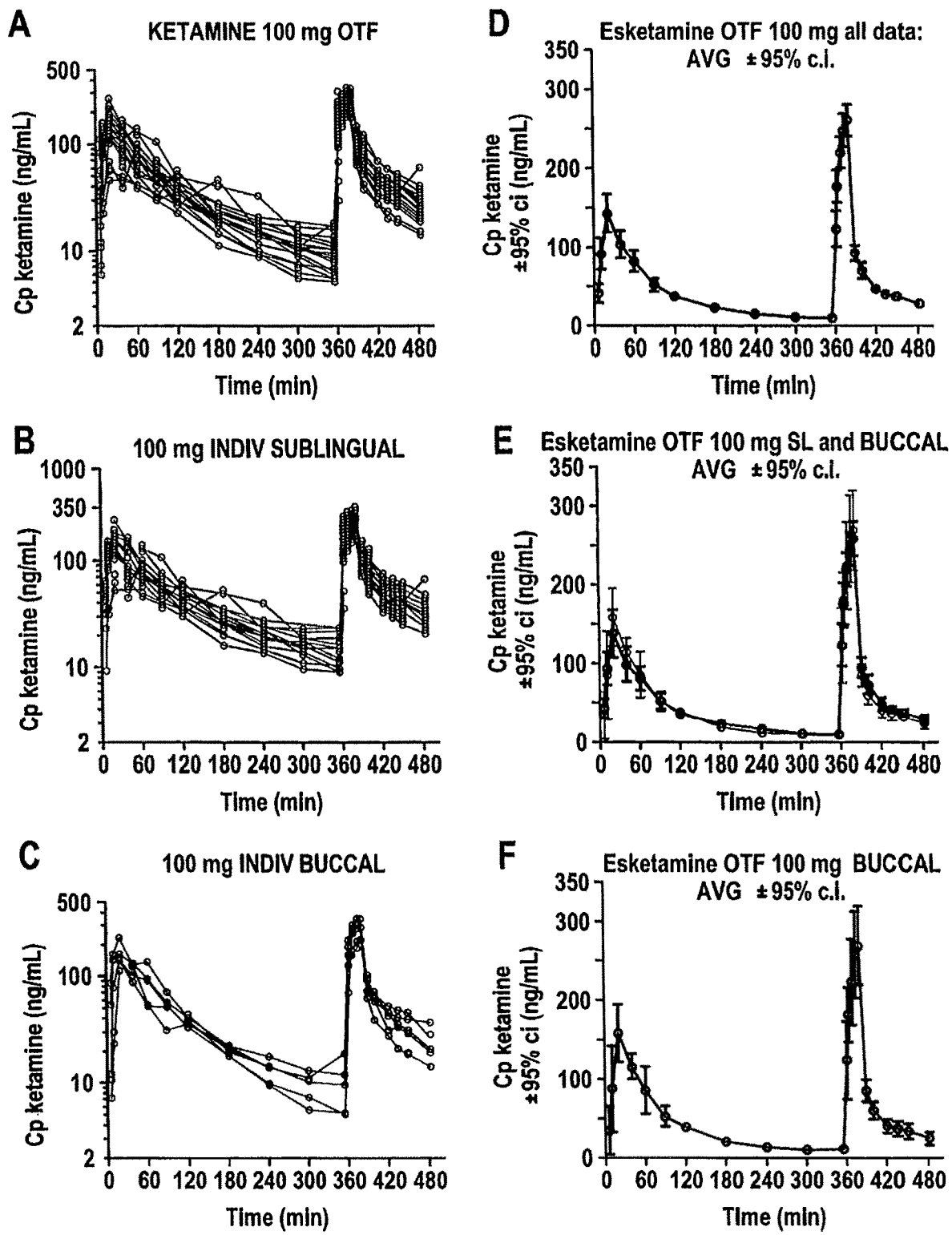
Figure 12:
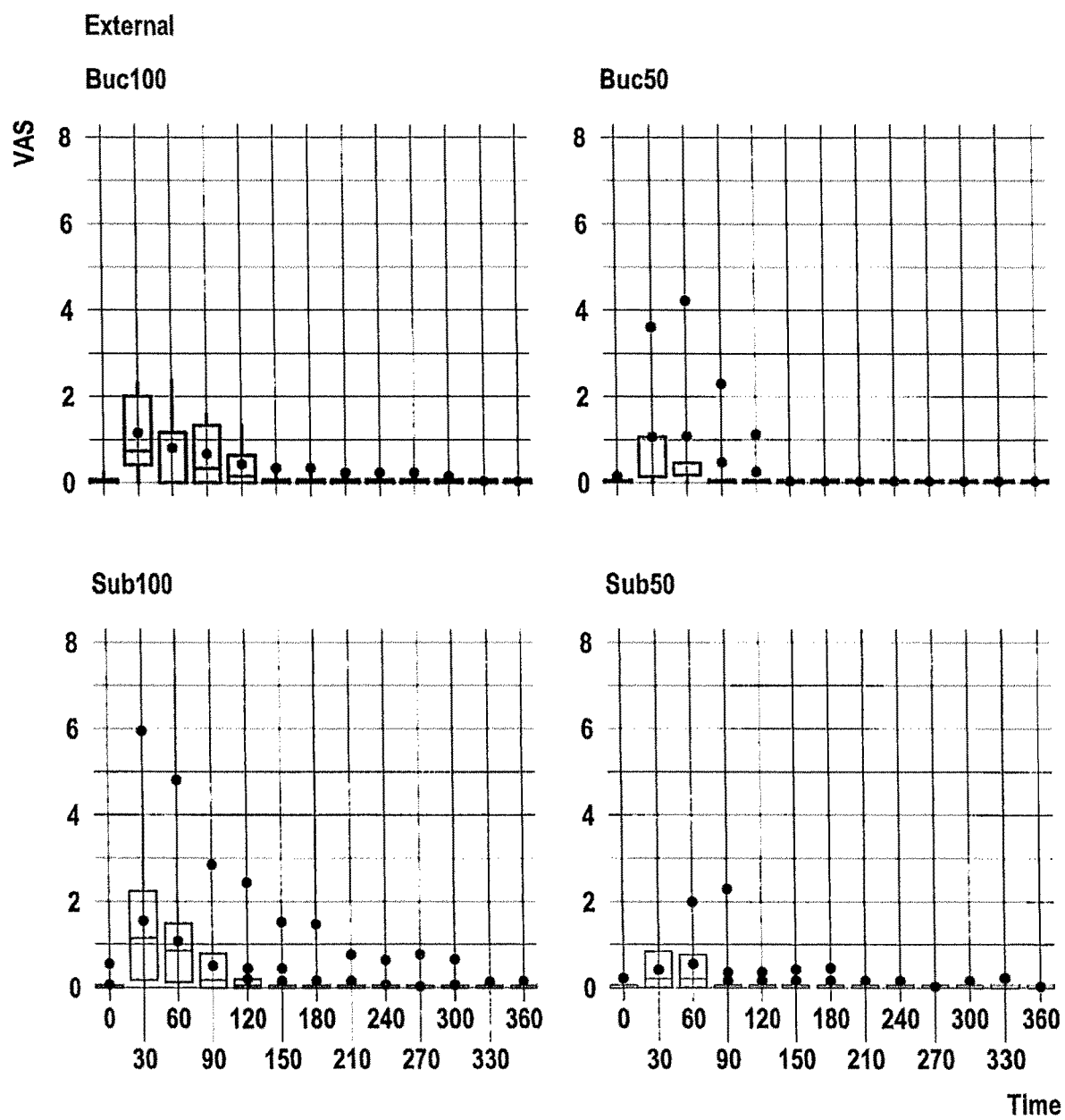
FIGS. 12-15 show the data relating to the observed psychedelic effects (phychological and psychomimetic side effects) according to the Bowdle questionnaire.
Figure 13:
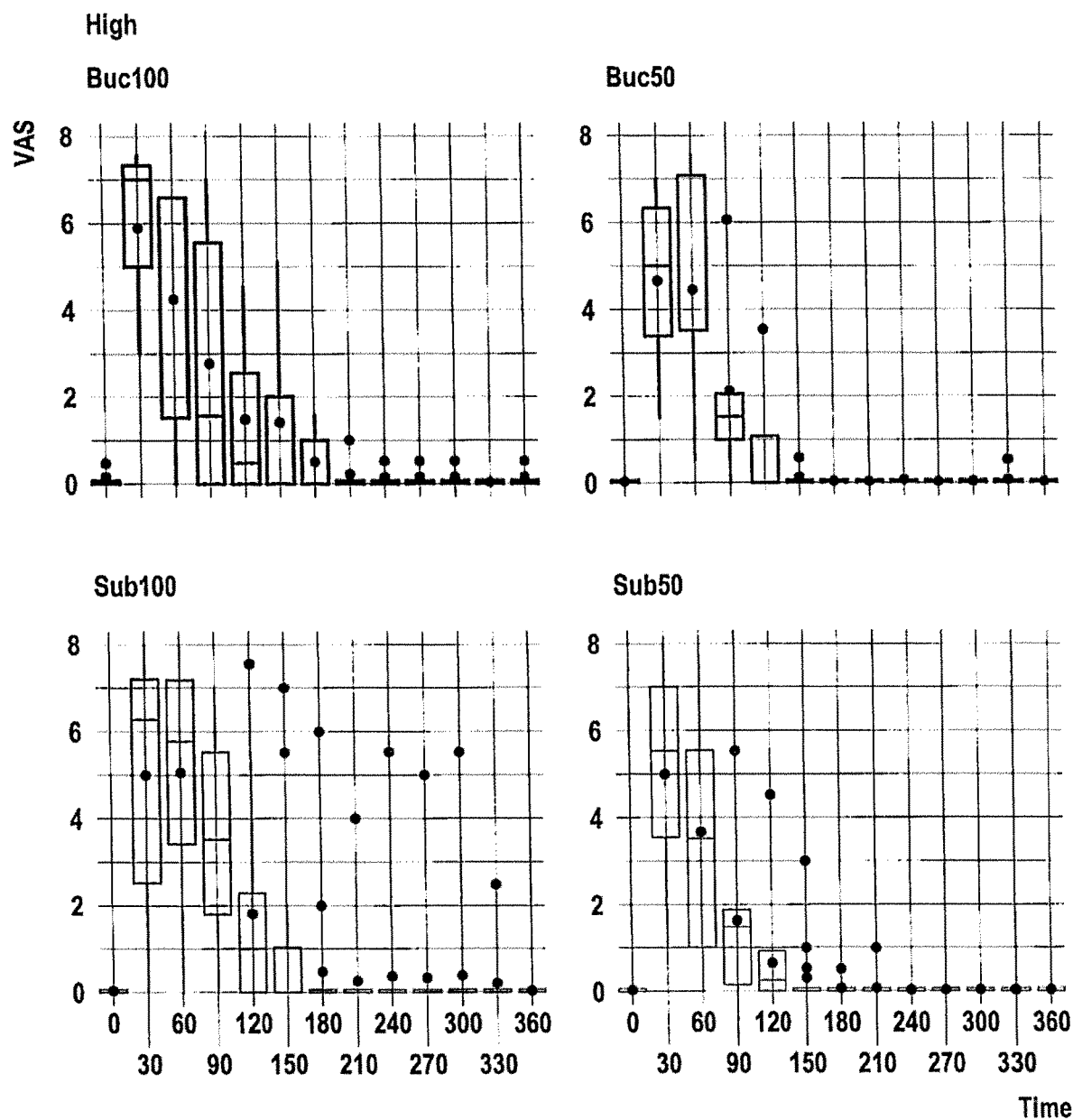
Figure 14:
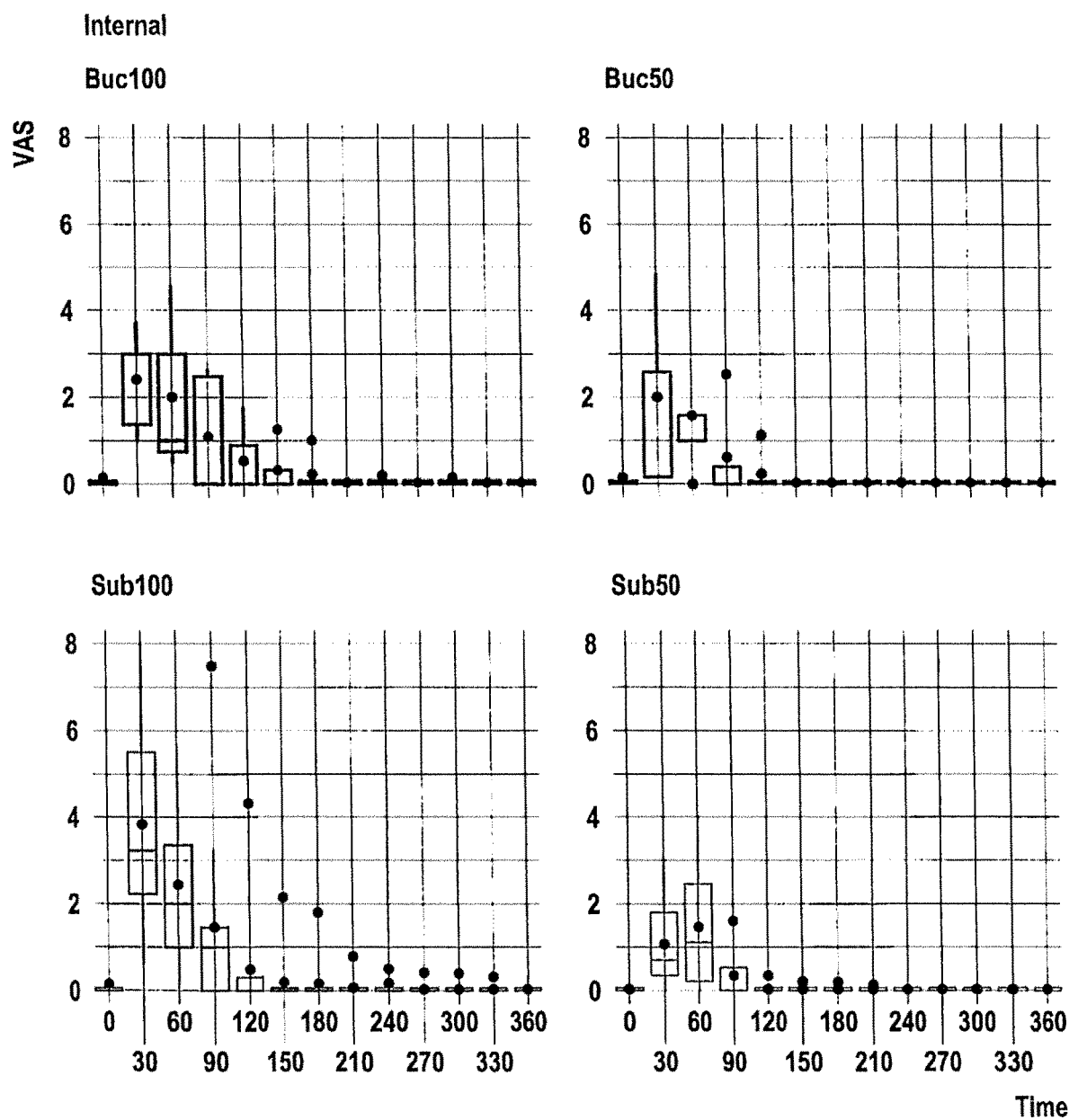
Figure 15:
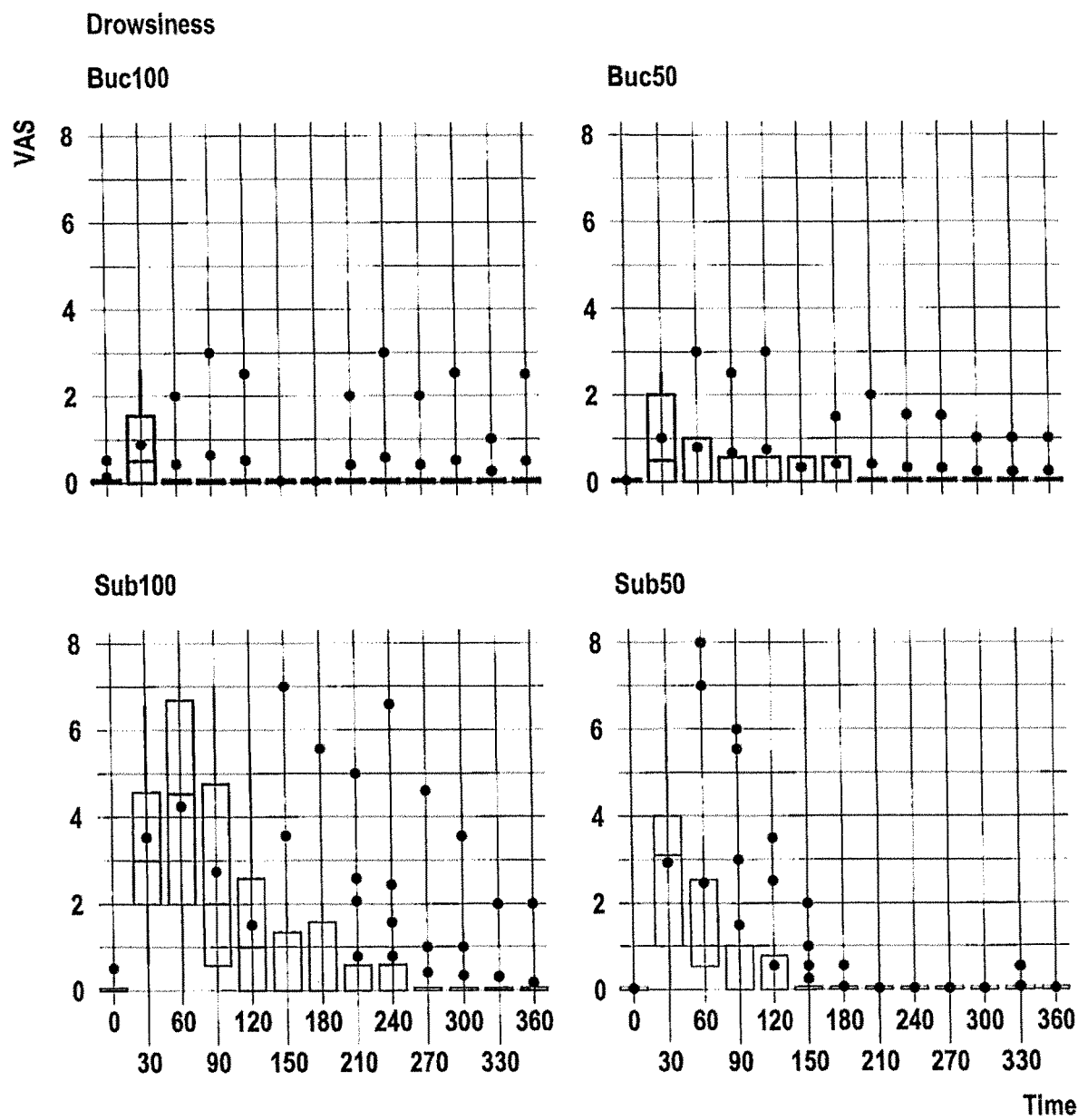
Figure 16:
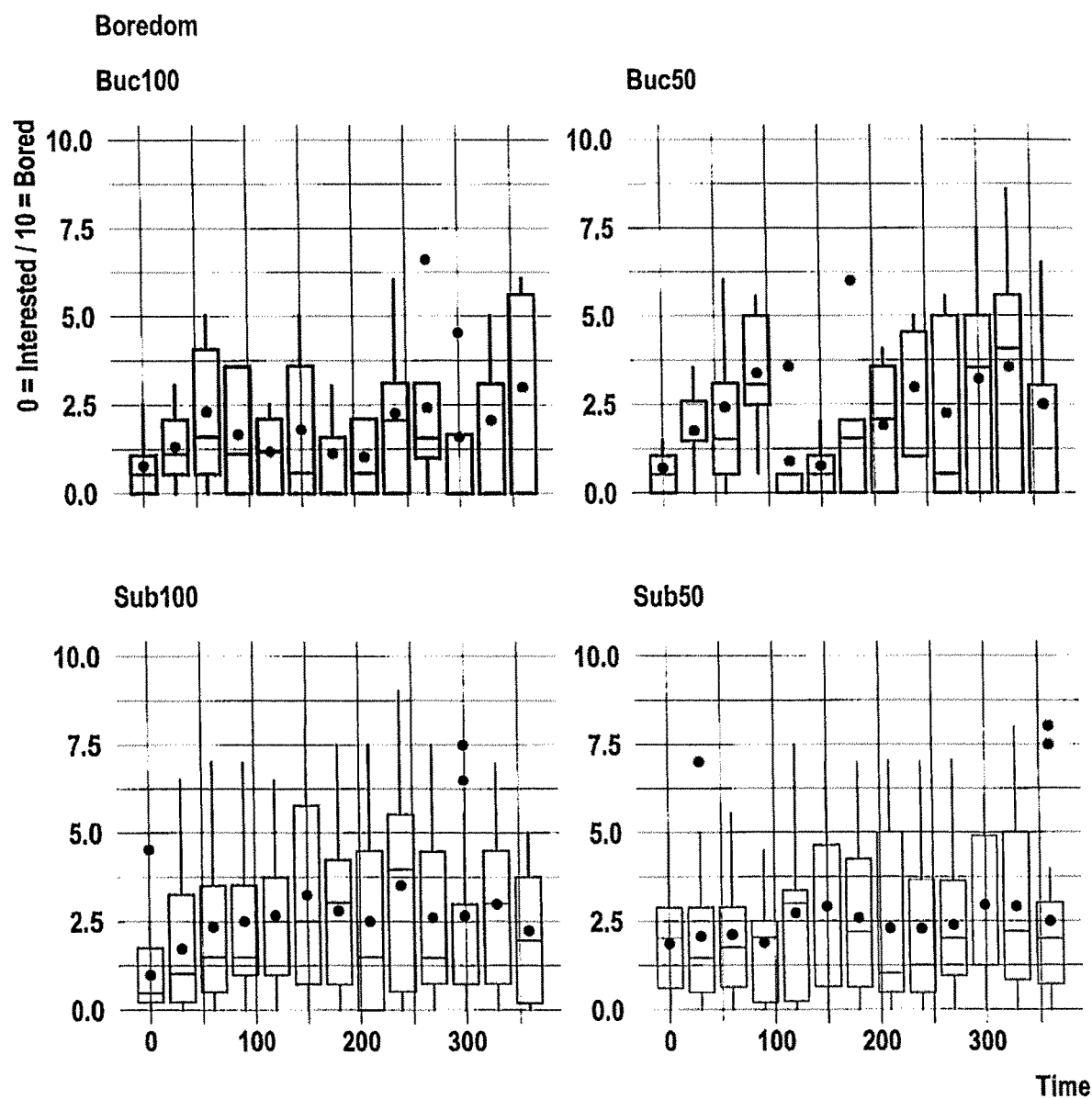
FIGS. 16-31 show the data relating response to the Bond and Lade questionnaire.
Figure 17:
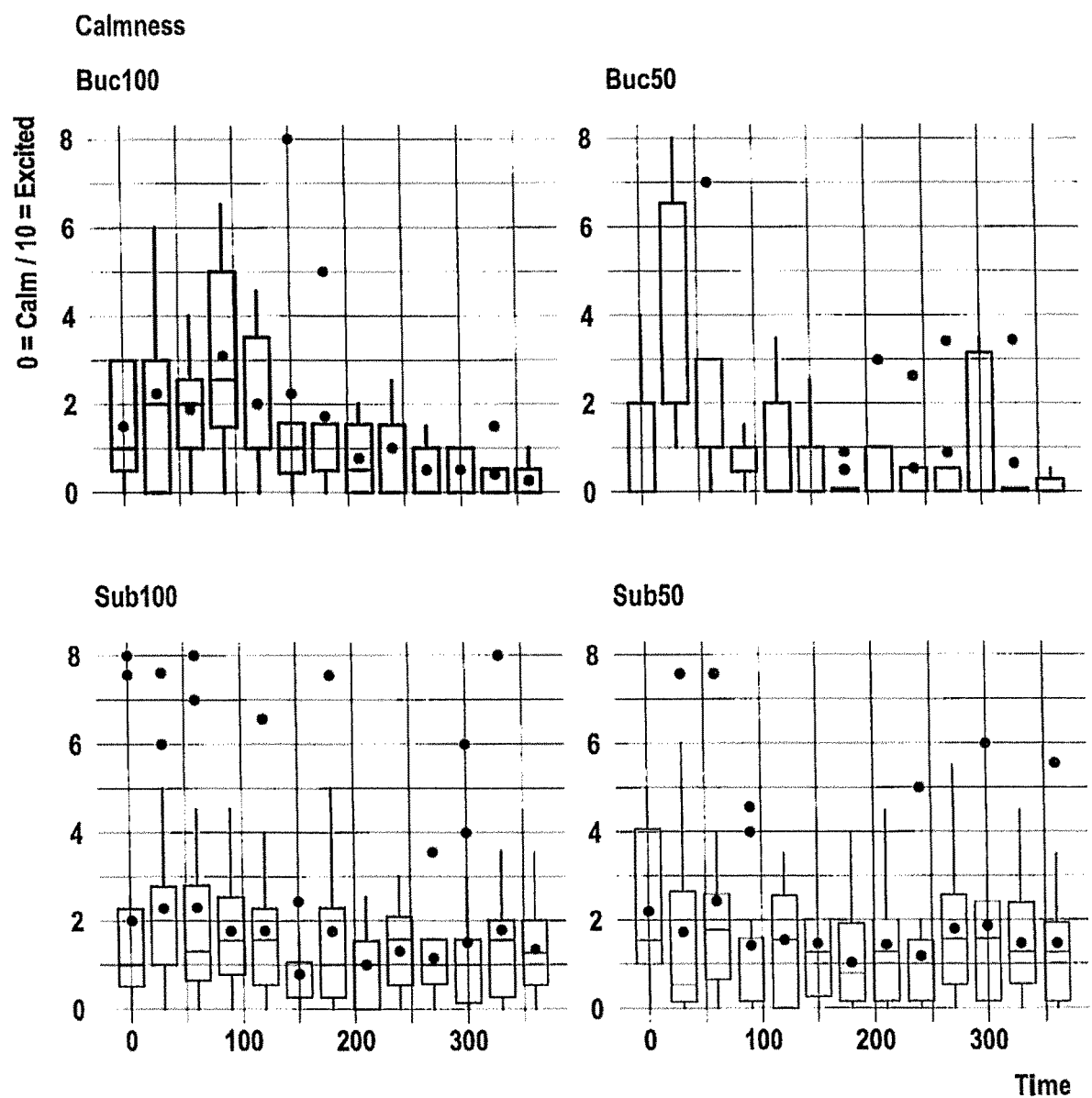
Figure 18:
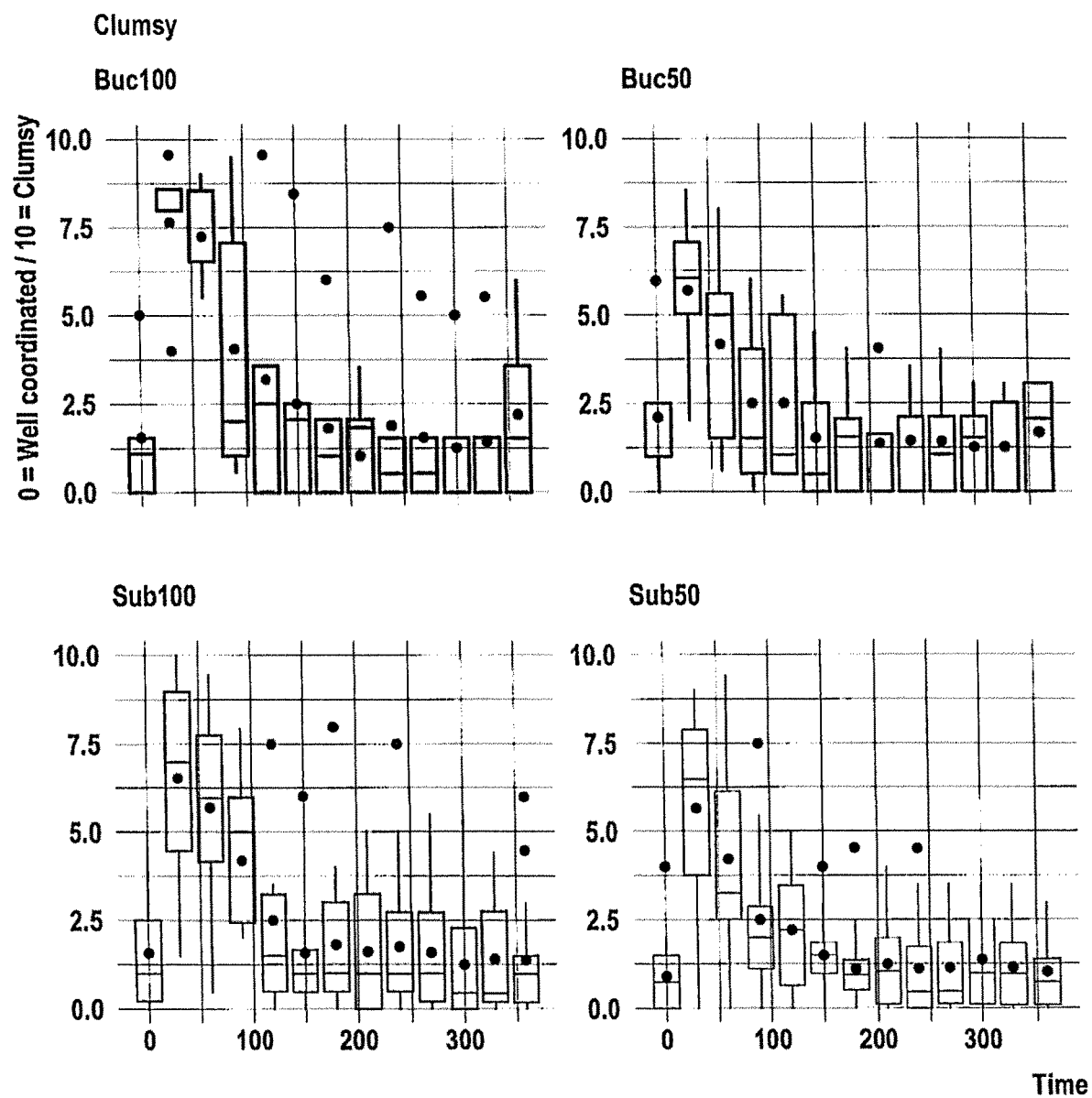
Figure 19:
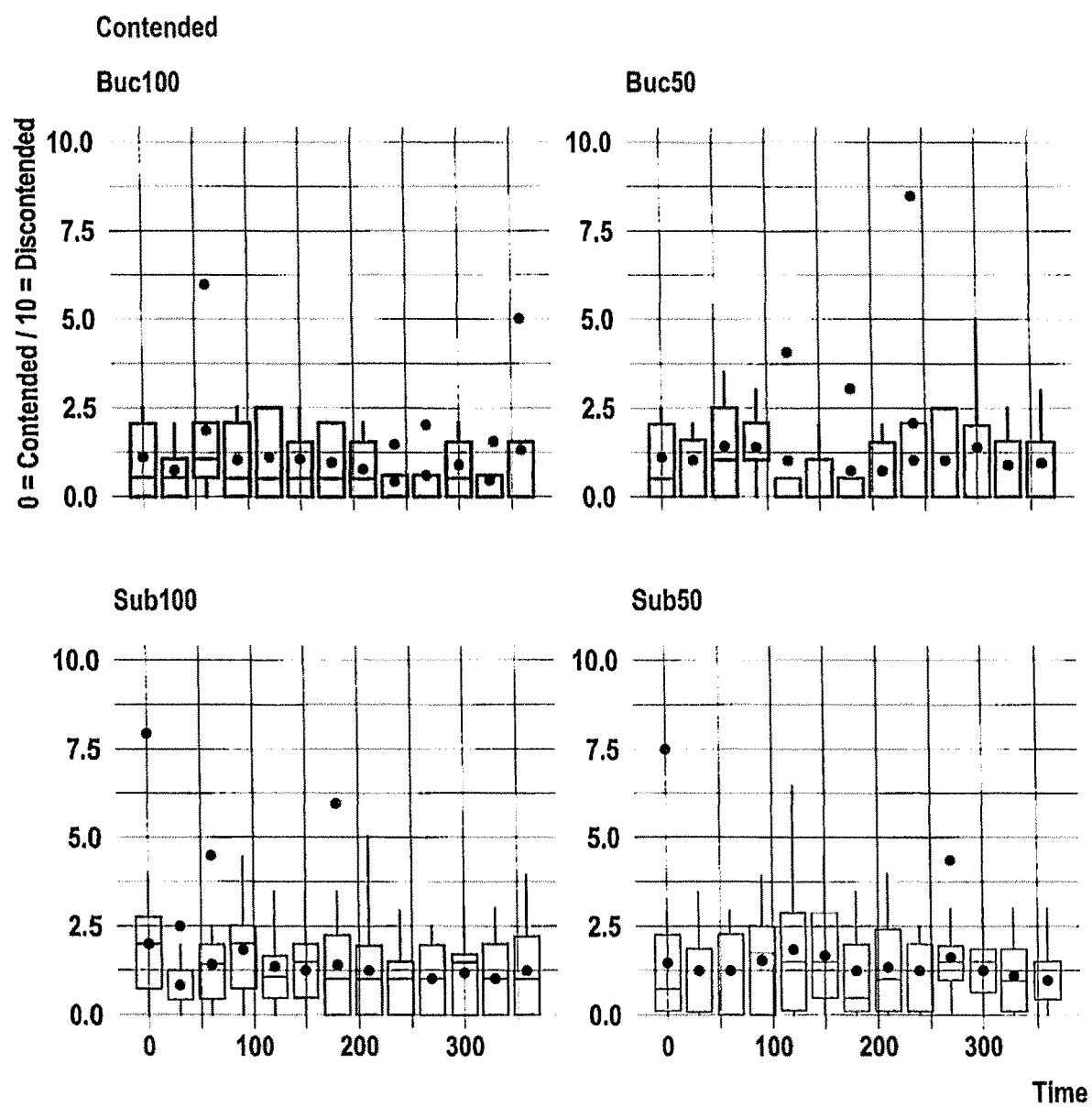
Figure 20:
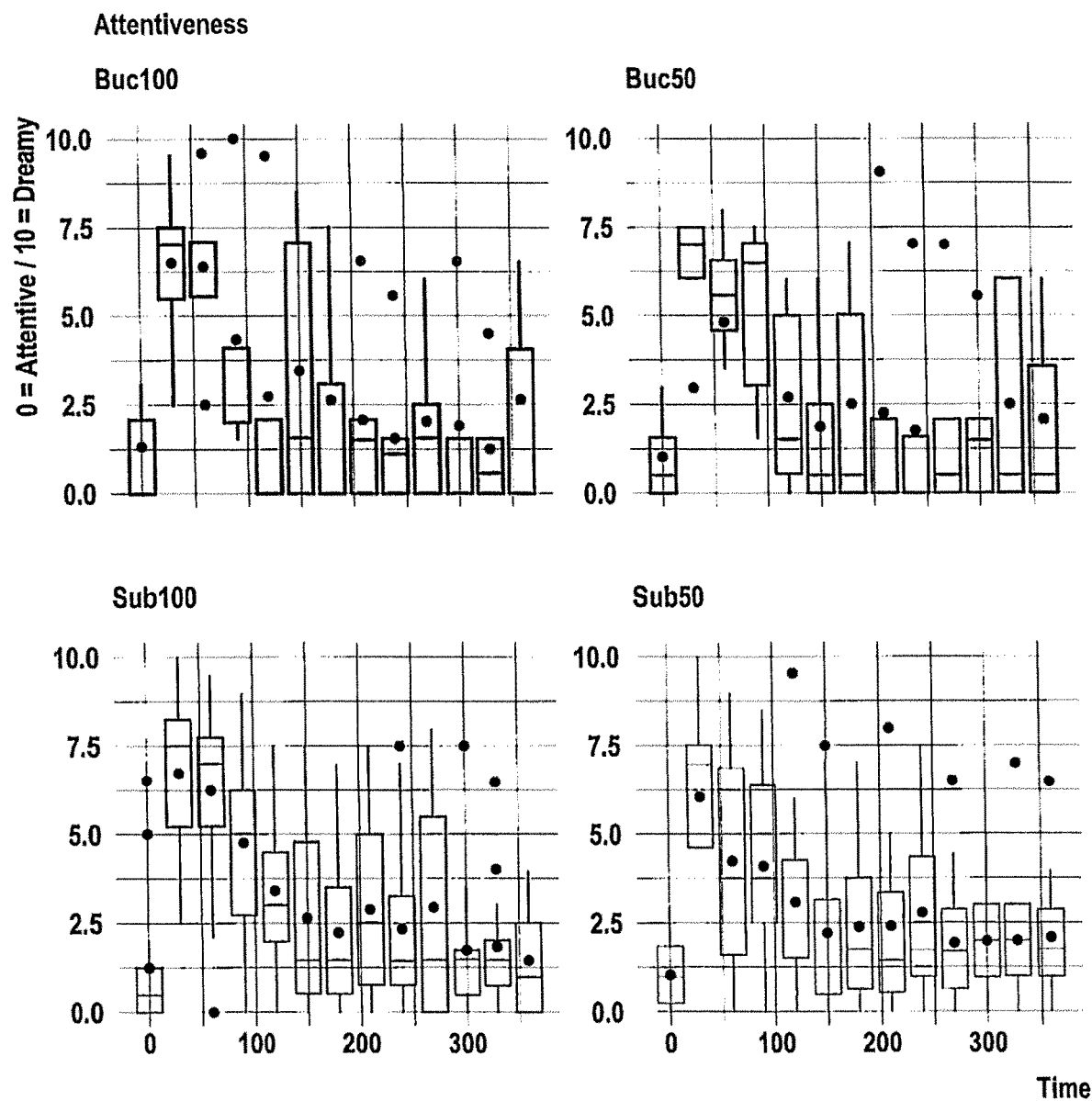
Figure 21:
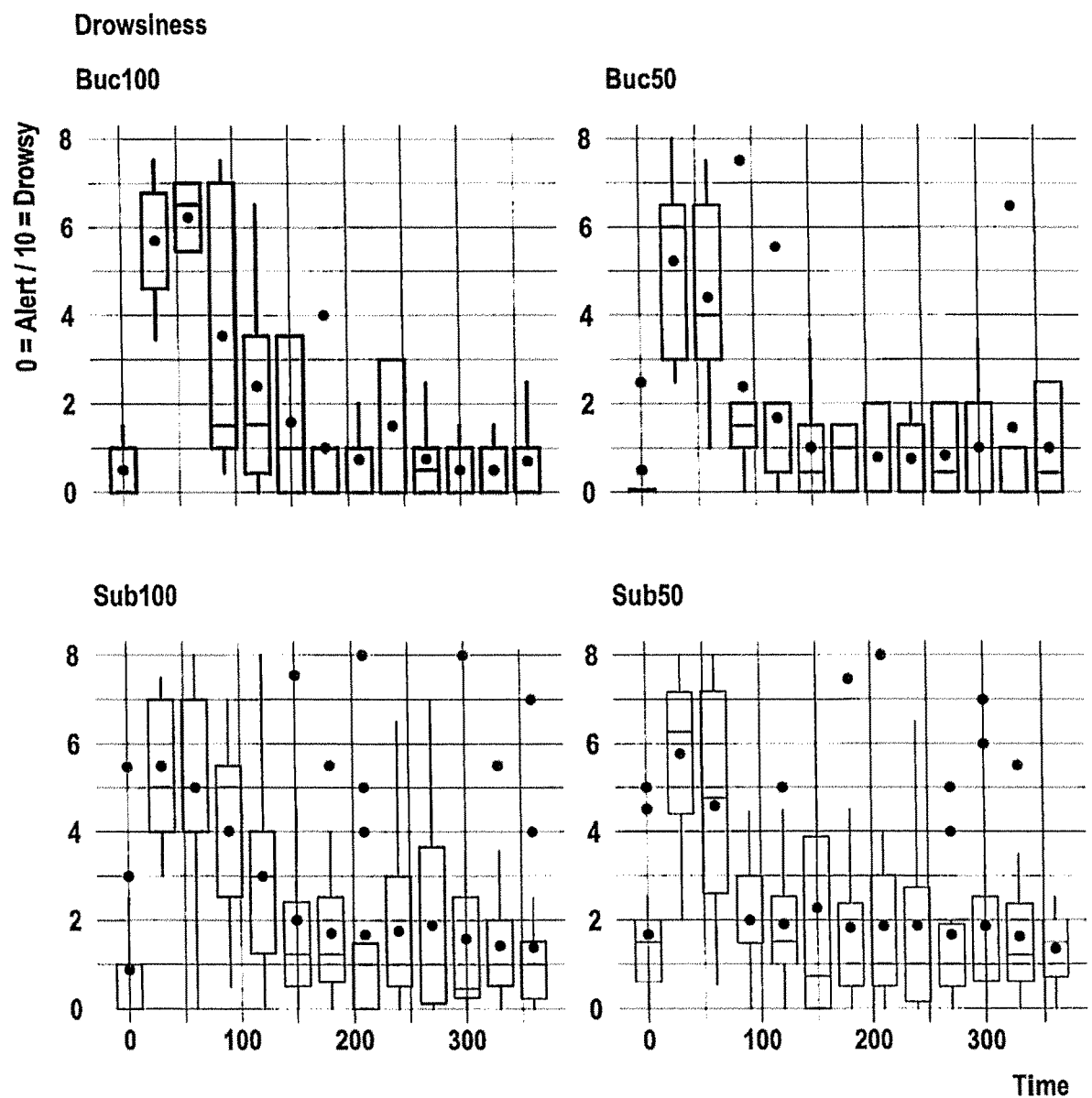
Figure 22:
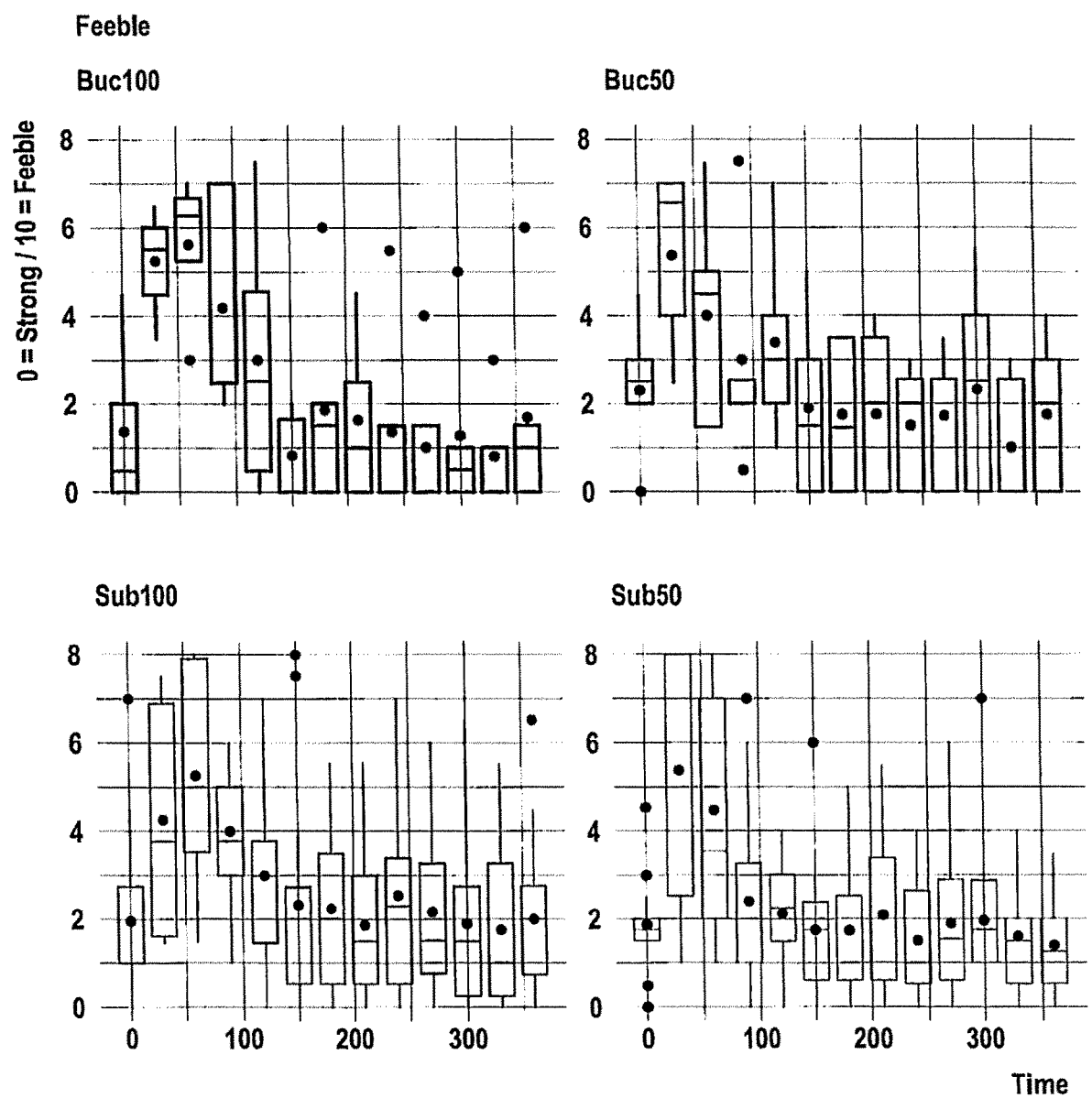
Figure 23:
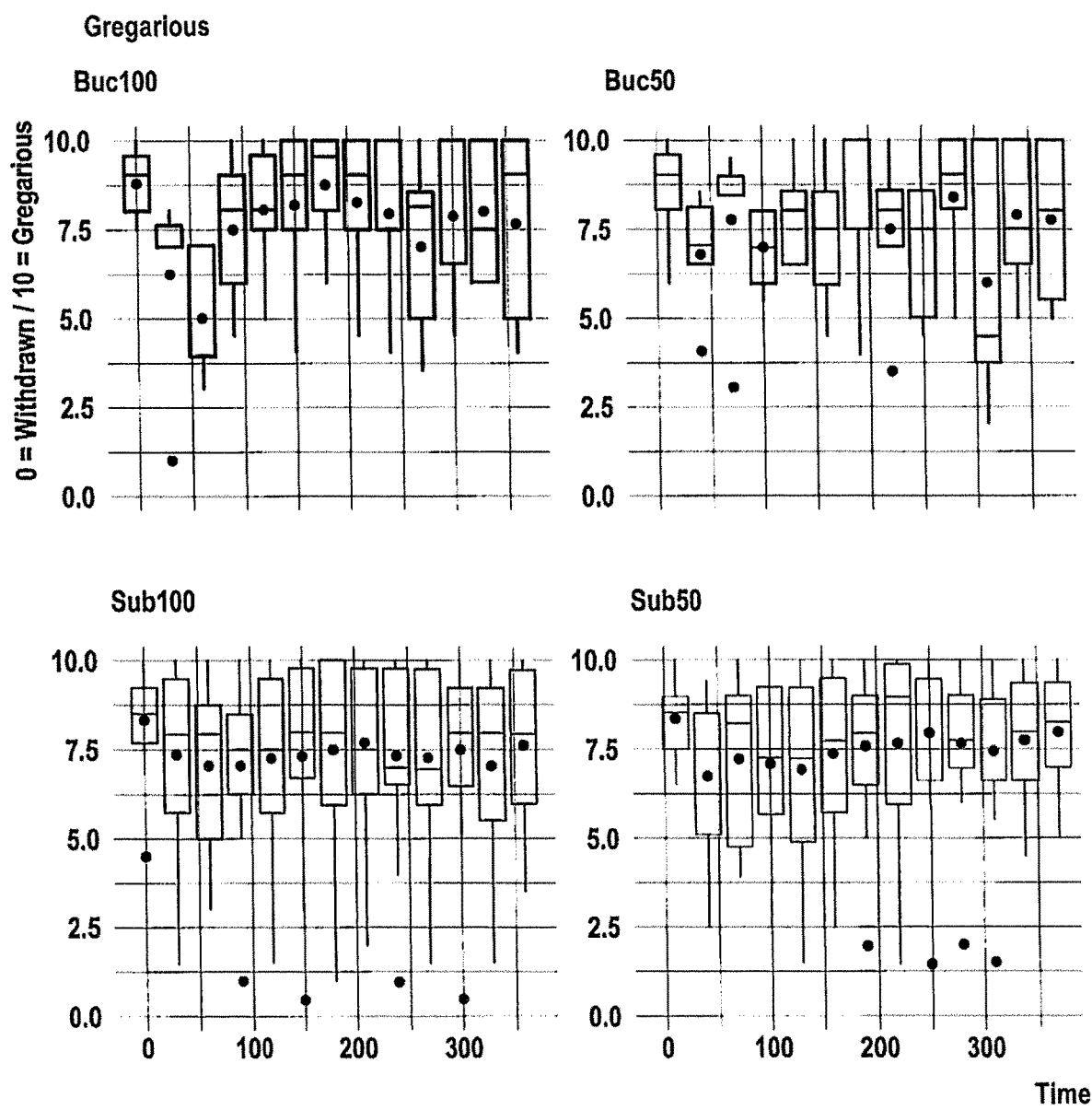
Figure 24:
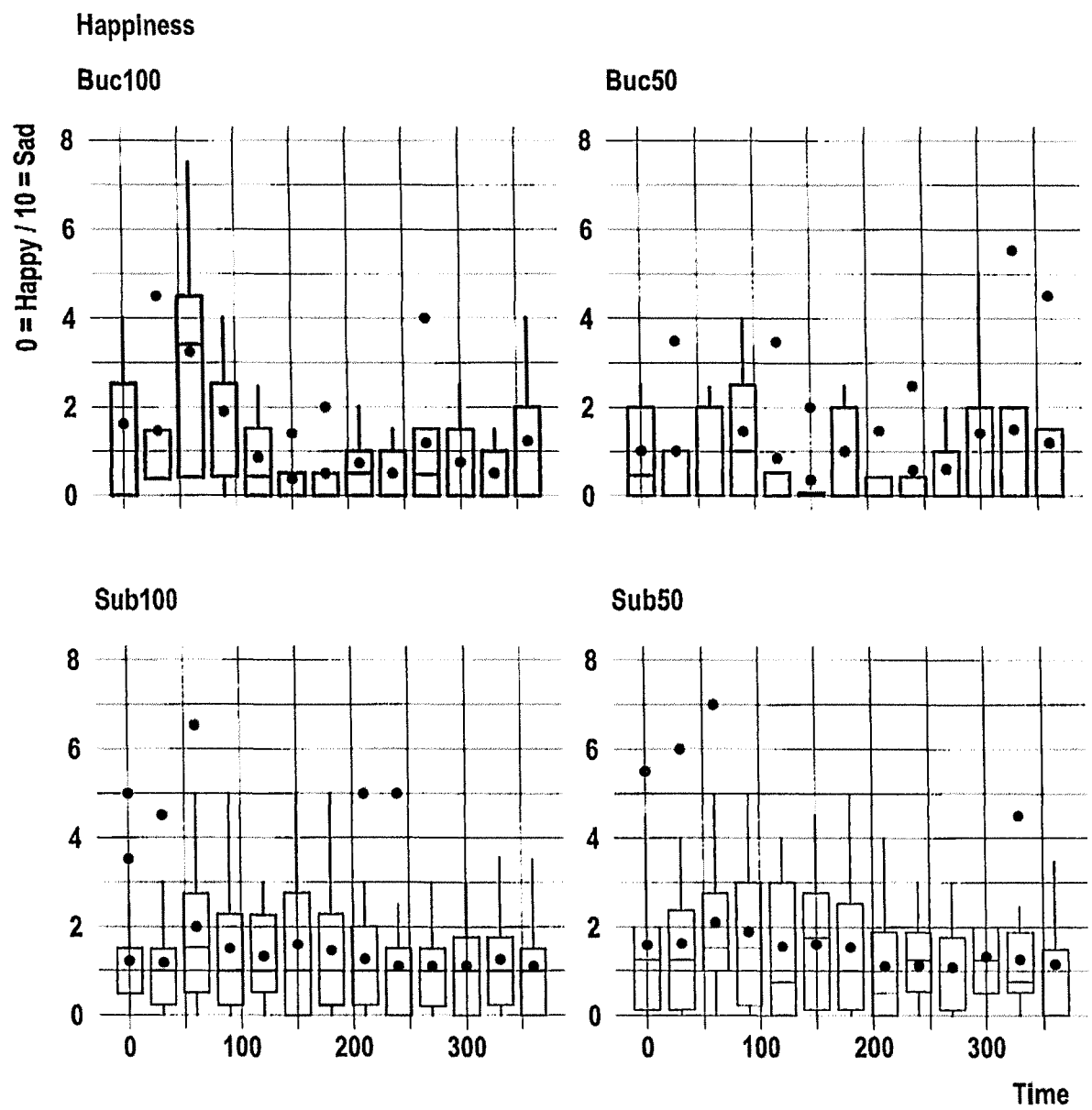
Figure 25:
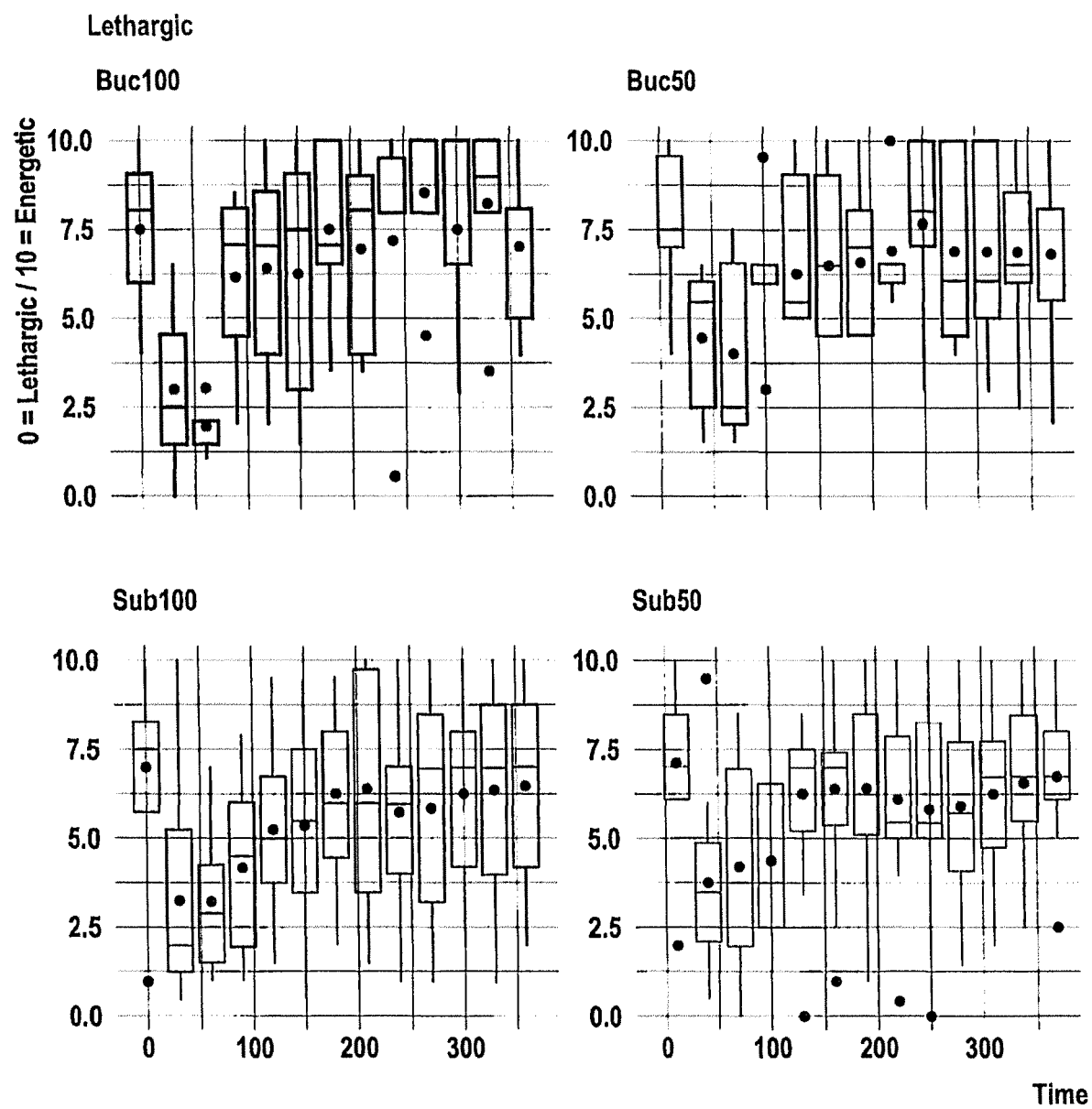
Figure 26:
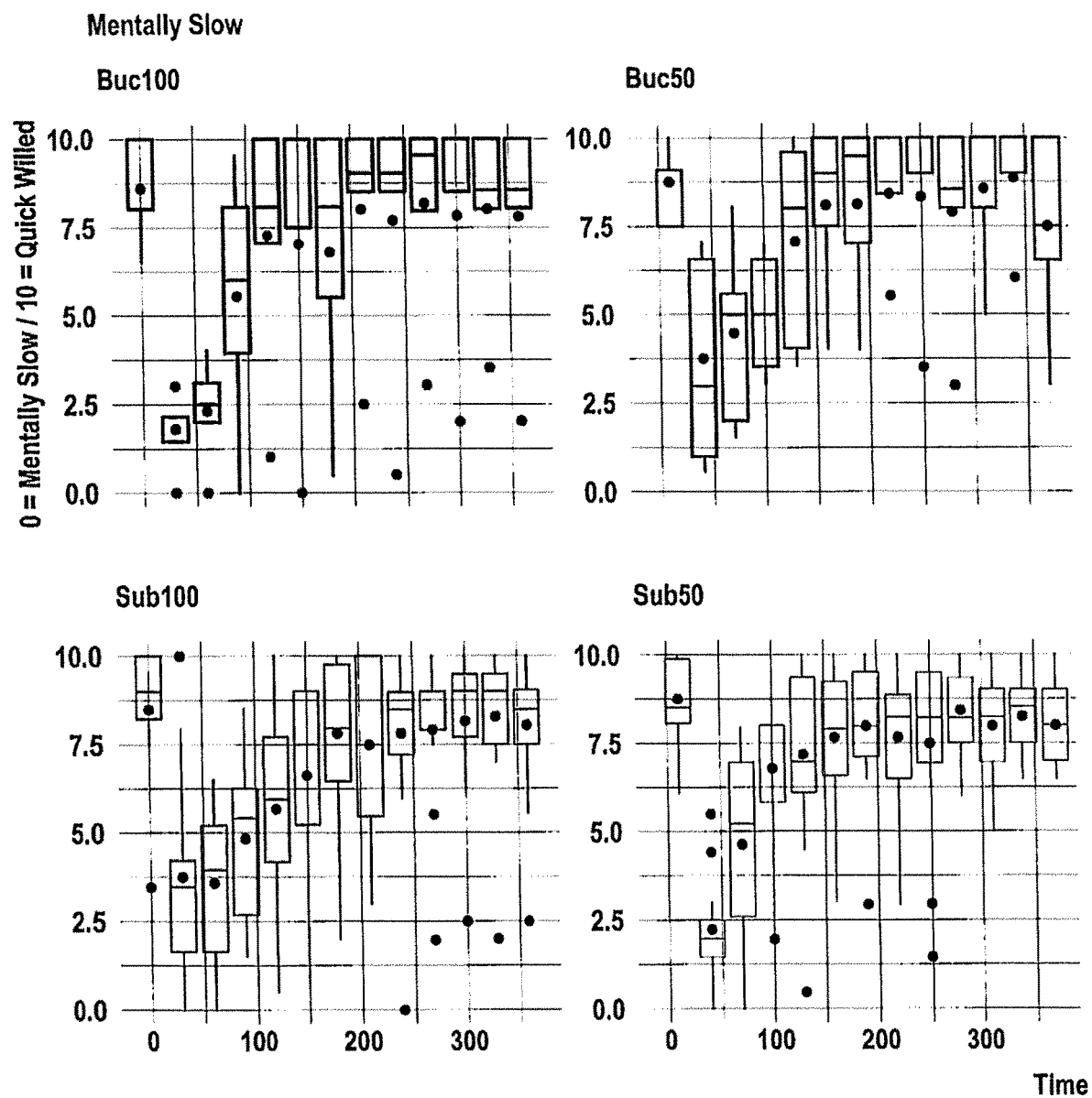
Figure 27:
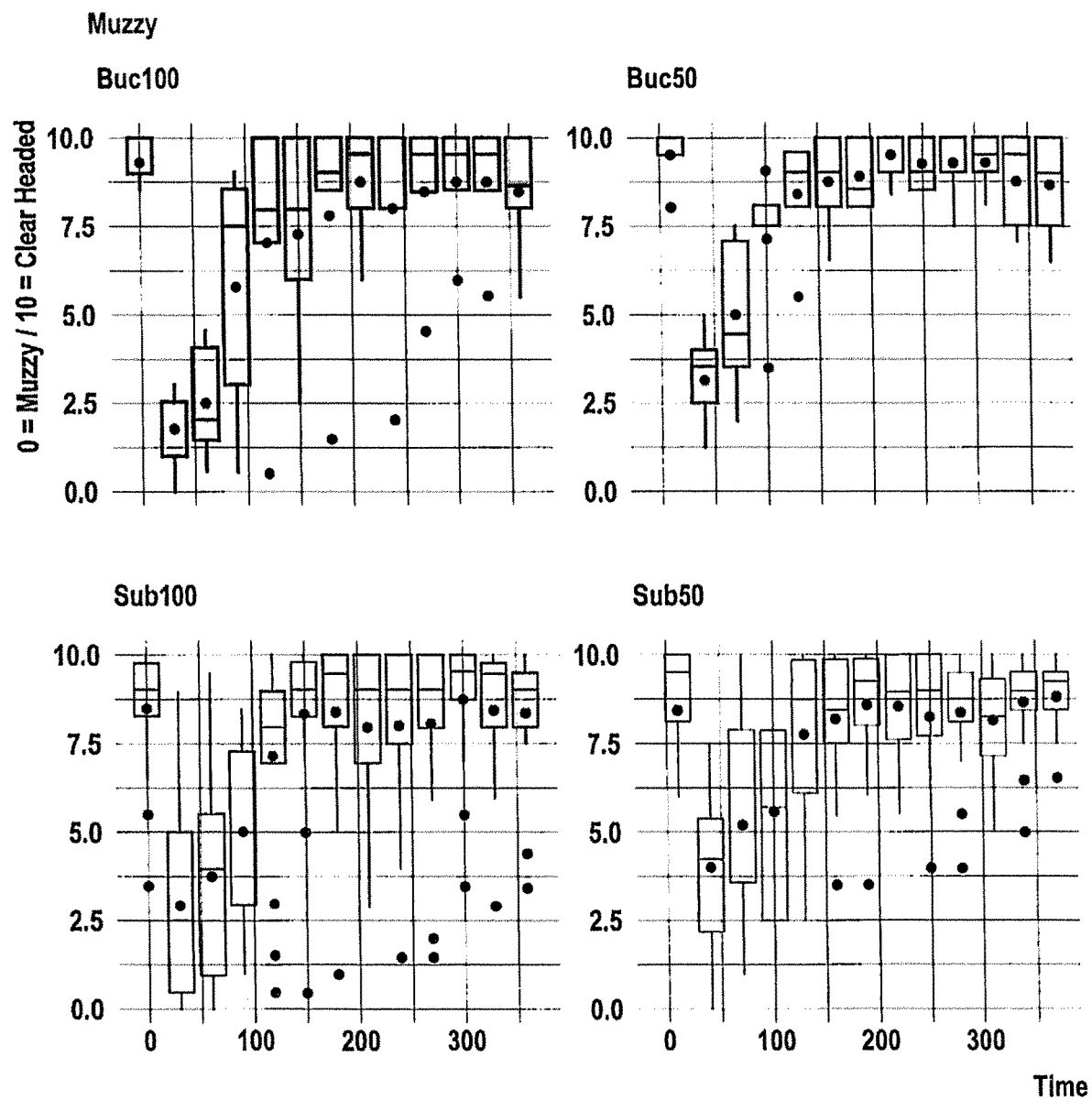
Figure 28:
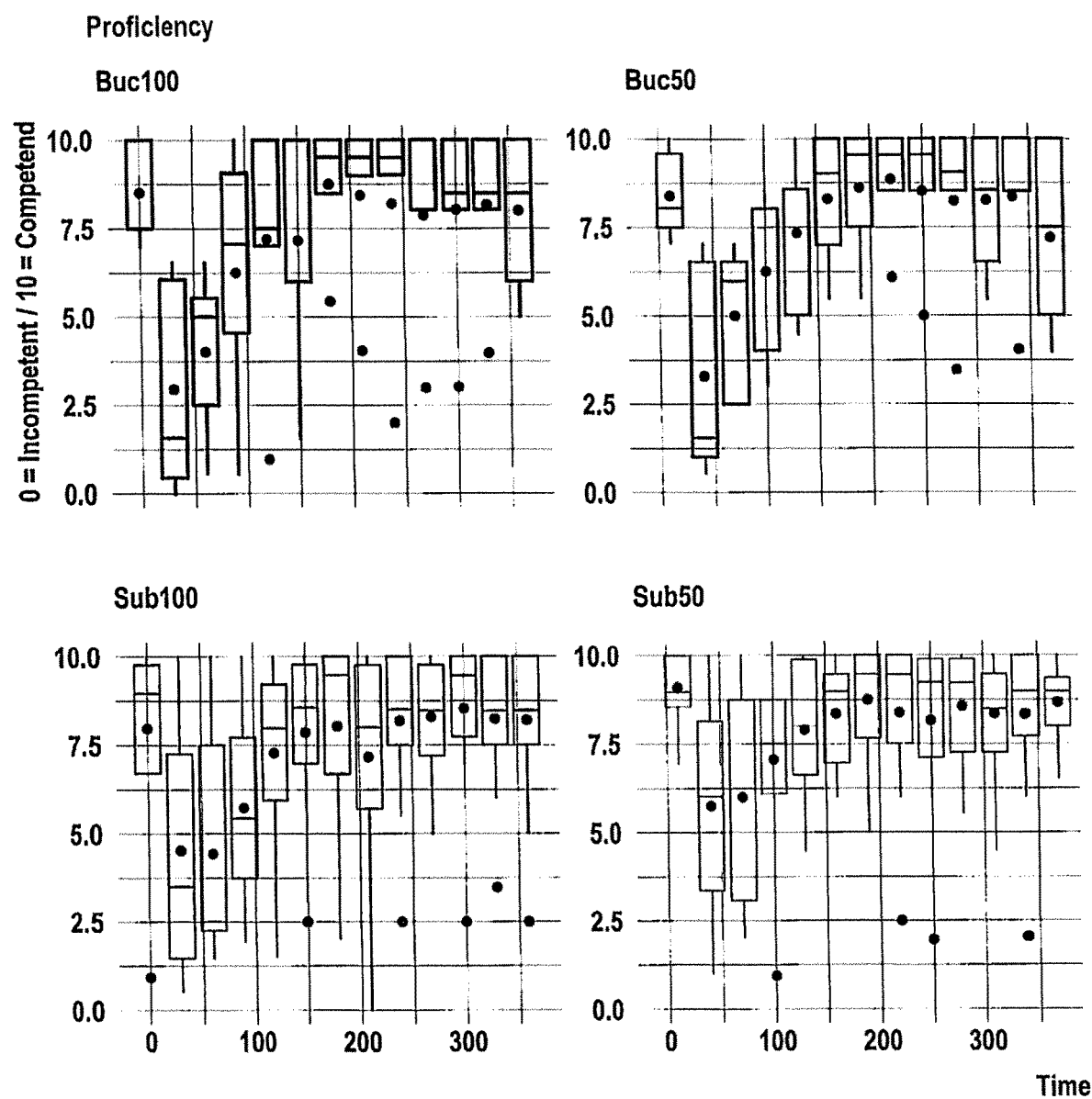
Figure 29:
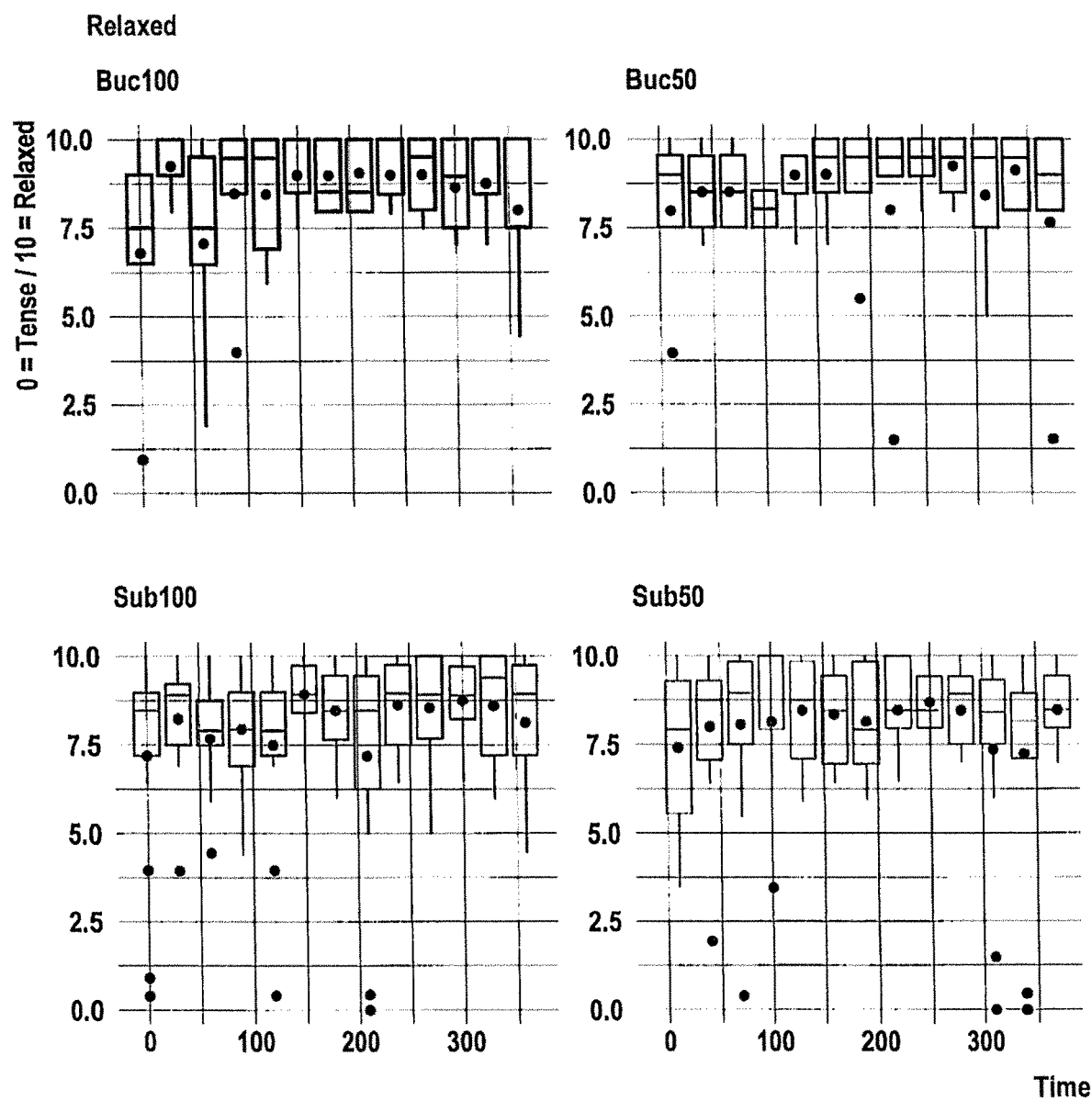
Figure 30:
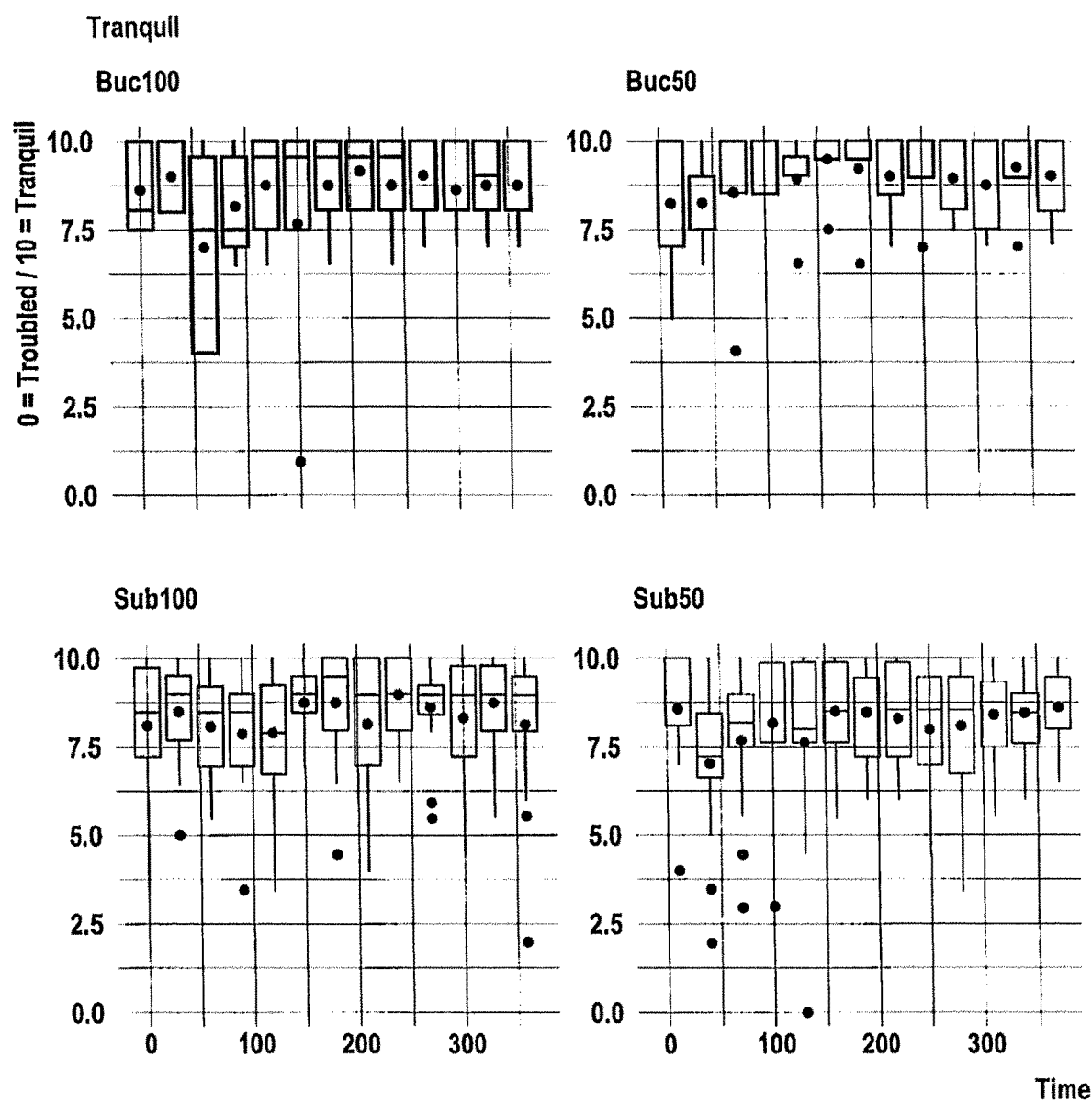
Figure 31:
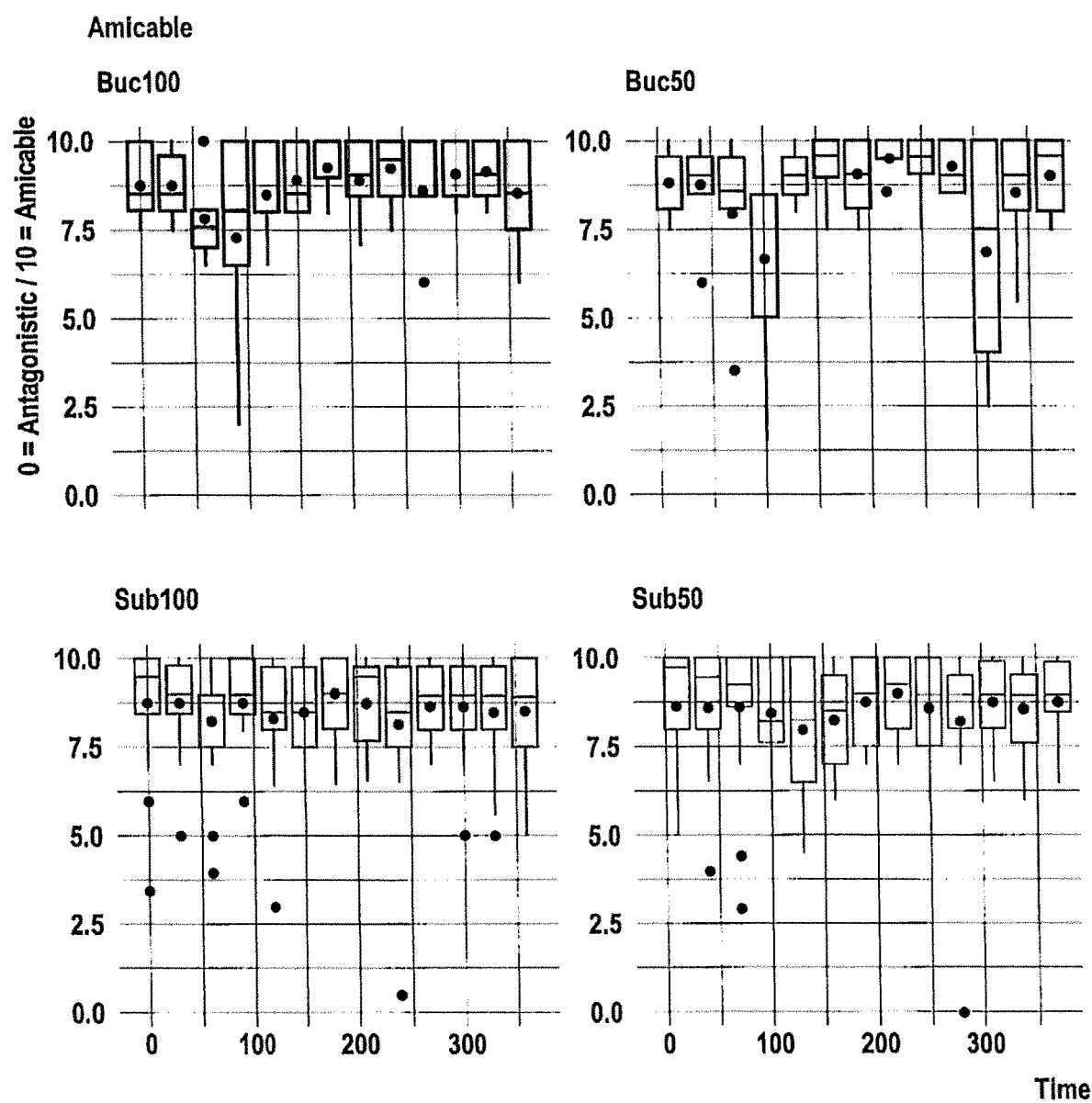

The plasma levels of ketamine are higher for intravenous administration than following administration of an OTF (see FIGS. 9, 10, 11 and Table 7 below).

The examined film formulation is suitable for the treatment of pain.

TABLE 7

| Cmax plasma concentration (ng/ml) | | | | | |
| --- | --- | --- | --- | --- | --- |
| All data 50 mg | All data 2 × 50 mg | Sublingually 50 mg | Sublingually 2 × 50 mg | Buccally 50 mg | Buccally 2 × 50 mg |
| (S)-ketamine 101 | 143 | 95 | 138 | 117 | 158 |
| (S)-Norketamine 254 | 330 | 258 | 323 | 242 | 450 |
| (S)-Hydroxy-norketamine 94 | 171 | 98 | 173 | 81 | 165 |

Following the administration of a film, the plasma values to be achieved are preferably in the following ranges: cmax ((S)-ketamine)=50-200 ng/mL; cmax ((S)-norketamine)= 200-400 ng/mL; cmax ((S)-hydroxynorketamine)=50-150 ng/mL.

If two films are administered, the plasma values to be achieved are preferably in the following ranges: cmax ((S)-ketamine)=100-200 ng/mL; cmax ((S)-norketamine) =300-500 ng/mL; cmax (hydroxynorketamine)=100-250 ng/mL.

Oral Bioavailability

The oral bioavailability for (S)-ketamine OTF is 26.3%±1.0%.

The oral bioavailability of 50 mg and 100 mg (S)-ketamine OTF differs by approximately 20% (F1 50 mg=29%, F1 100 mg=23%), but this does not reach the significance level ($p \gg 0.01$).

Tmax, AUC data calculated using a PK model.

Data analysis of measured plasma concentrations of (S)-ketamine and its metabolites to determine a pharmacokinetic model was performed using NONMEM version 7.5.0 (ICON Development Solutions, Hanover, MD, USA).

FOCI-I (first-order conditional estimation with interaction) was used to calculate the pharmacokinetic model parameters. Based on the created pharmacokinetic model, TMax data and AUC data of (S)-ketamine and its metabolites were calculated and are shown in Table 8.

TABLE 8

| | 50 mg (S)-Ketamine OTF | 100 mg (S)-Ketamine OTF |
| --- | --- | --- |
| | (S)-Ketamin | |
| Tmax (min) | 18.8 (16.6-21.2) | 19.1 (17.1-21.2) |
| AUC (0-6) (ng/mL · min) | 8.363 (7.263-9.464) | 13.347 (11.933-14.760) |
| | (S)-Norketamine | |
| Tmax (min) | 61 (53-68) | 78 (66-91) |
| AUC (0-6) (ng/mL · min) | 38.497 (34.131-42.863) | 67.959 (60.045-75.872) |
| | (S)-Hydroxynorketamine | |
| Tmax (min) | 81 (69-92) | 109 (89-130) |
| AUC (0-6) (ng/mL · min) | 24.087 (20.694-27.480) | 44.972 (38.563-51.382) |

Further results of the study are as follows:
1. The OTF formulation according to the invention has an analgesic effect in all three pain modalities, irrespective of the localisation.
2. None of the used pain tests showed a clear dose-effect relationship.
3. In the electrical and thermal pain test, the analgesic effect is long-lasting and ranged from 2 to 6 hours, especially following sub-lingual administration of the OTF.
4. There are no obvious differences in the data obtained during and after sublingual and buccal administration.
5. The psychedelic effects for the administered OTF can be considered to be very mild.
6. Eighteen (18) test subjects reported at least one adverse event. In total, there were 33 adverse events. None of these was a serious adverse event (see Table 9 below for the prevalence of the events). The adverse events were observed primarily for the intravenous administration of 20 mg (S)-ketamine.

TABLE 9

| Side effect | 50 mg (S)-ketamine | 100 mg (S)-ketamine | 20 mg (S)-ketamine IV |
| --- | --- | --- | --- |
| Blurred vision | 1 | — | — |
| Feeling of drunkenness | 2 | — | — |
| Bradykinesia | 1 | 1 | — |
| Whistling noise in the ear | — | — | 1 |
| Dizziness | 1 | 3 | 4 |

TABLE 9-continued

| Side effect | 50 mg (S)-ketamine | 100 mg (S)-ketamine | 20 mg (S)-ketamine IV |
|---|---|---|---|
| Drowsiness | — | — | 3 |
| Nausea | 1 | 1 | 2 |
| Headache | 1 | 2 | 3 |
| Numbness of the tongue | | 2 | — |
| High blood pressure (SBP > 180 mm Hg) | — | — | 2 |
| Sweating | — | — | 1 |
| Dry eyes | — | — | 1 |
| Total | 7 | 9 | 17 |

The data relating to the observed psychedelic effects (psychological and psychomimetic side effects) according to the Bowdle questionnaire are summarised in FIGS. 12 to 15 and according to the Bond and Lade questionnaire are summarised in FIGS. 16 to 31.

Example 5

The active agents R-ketamine and (S)-ketamine were compared.

To this end, oral thin films with the composition according to Table 10 were produced.

TABLE 10

| Material | 15 [wt. %] | 16 [wt. %] |
|---|---|---|
| S ketamine HCl | 60.0 | |
| R-ketamine HCl | | 60.0 |
| PVA 4-88 | — | — |
| PVA 40-88 | 10.0 | 10.0 |
| Kollicoat IR | 20.1 | 20.1 |
| Saccharin Na | 1.0 | 1.0 |
| Sucralose | 2.0 | 2.0 |
| Glycerol | 3.5 | 3.5 |
| Cherry Flavour M55394 | 3.0 | 3.0 |
| FD&C Red No, 40 | 0.4 | 0.4 |
| Solvent | Aq. Pur. | Aq. Pur. |
| Area density | 215.73 g/m² | 221.4 g/m² |

The active agent flux was determined below in the in vitro model.

The active agent flux was performed within the scope of a typical in vitro permeation by means of Franz diffusion cells (volume 10 mL) at 37° C. The used acceptor medium was replaced completely for a new one at predetermined replacement times, and the content of permeated active agent amount in these acceptor solutions was determined by means of HPLC.

Phosphate buffer (pH 7.4) was used as acceptor medium.

Dermatomised skin from the oesophagus of a pig with a layer thickness of 400 µm was used as skin model.

Figure 32:
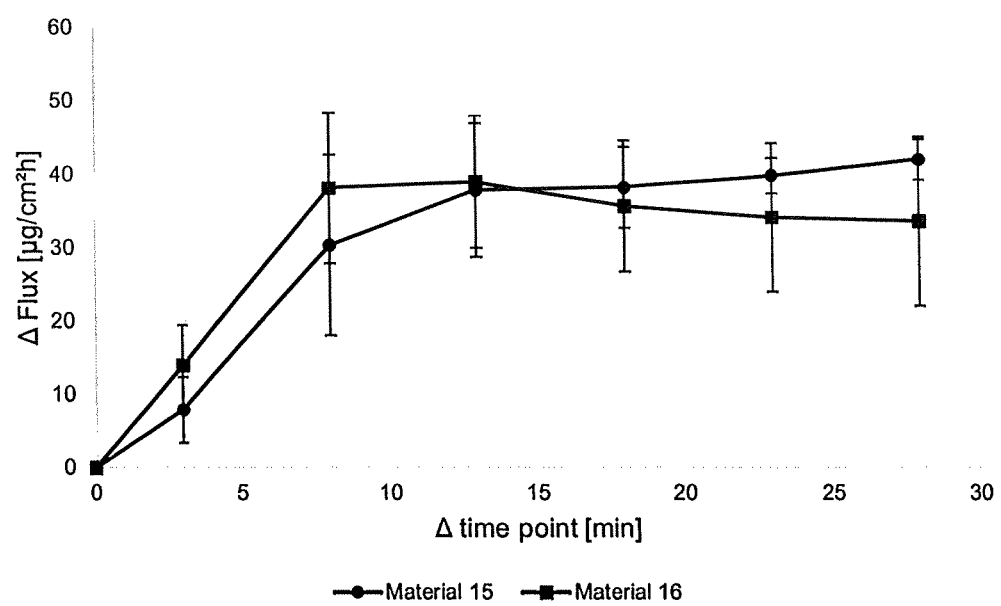
FIG. 32 shows the results of the permeation study of Example 5.

The results of the permeation study are shown in FIG. 32.

The invention claimed is:

1. An oral thin film comprising at least one matrix layer, wherein the at least one matrix layer comprises ketamine in an amount of 45 to 70 wt. %, in relation to the total weight of the matrix layer, at least one polyvinyl alcohol with a mean molecular weight of 200,000 to 210,000 g/mol, in an amount of 5 to 40 wt. % in relation to the total weight of the matrix layer, and at least one polyvinyl alcohol-polyethylene glycol graft copolymer in an amount of 15 to 45 wt. % in relation to the total weight of the matrix layer.

2. The oral thin film according to claim 1, wherein ketamine comprises a pharmaceutic ally acceptable salt of ketamine.

3. The oral thin film according to claim 1, wherein the matrix layer further includes at least one polyvinyl alcohol with a mean molecular weight of approximately 25,000 to approximately 35,000 g/mol.

4. The oral thin film according to claim 1, wherein the at least one polyvinyl alcohol-polyethylene glycol graft copolymer has a polyethylene glycol main chain onto which there are grafted polyvinyl alcohol units.

5. The oral thin film according to claim 1, wherein the at least one polyvinyl alcohol-polyethylene glycol graft copolymer has a polyethylene glycol main chain onto which there are grafted polyvinyl alcohol units, wherein the molar ratio of polyethylene glycol to polyvinyl alcohol is 1:3.

6. The oral thin film according to claim 1, wherein the at least one polyvinyl alcohol-polyethylene glycol graft copolymer has a polyethylene glycol main chain onto which there are grafted polyvinyl alcohol units, wherein the polyvinyl alcohol-polyethylene glycol graft copolymer has a mean molecular weight in the range of 40,000 to 50,000 g/mol.

7. The oral thin film according to claim 1, wherein the oral thin film further comprises at least one auxiliary substance selected from the group comprising colouring agents, flavourings, sweeteners, plasticisers, taste-masking agents, emulsifiers, enhancers, pH regulators, humectants, preservatives and/or antioxidants.

8. The oral thin film according to claim 1, wherein the area density of the oral thin film is approximately 50 to 300 g/m.

9. The oral thin film according to claim 1, wherein the ketamine comprises ketamine as a free base in a total amount of 25 to 150 mg.

10. The oral thin film according to claim 1, wherein at least 40% of the ketamine is released within the first minute following application, and/or wherein at least 75% of the ketamine is released within the first two minutes following application.

11. The oral thin film according to claim 1, wherein the puncture strength is at least 0.15 N/mm with an areal density of 150 to 250 g/m.

12. The oral thin film according to claim 1, wherein the matrix layer comprises 60 wt. % of (S)-ketamine HCl, 10 wt. % of a polyvinyl alcohol with a mean molecular weight of approximately 200,000 to 210,000 g/mol, and 20.1 wt. % of a polyvinyl alcohol-polyethylene glycol graft copolymer, wherein the polyvinyl alcohol-polyethylene glycol graft copolymer has a polyethylene glycol main chain onto which there are grafted polyvinyl alcohol units, and wherein the polyvinyl alcohol-polyethylene glycol graft copolymer has a mean molecular weight in the range of 40,000 to 50,000 g/mol.

13. The oral thin film according to claim 1, wherein the maximum plasma concentration of (S)-ketamine following administration of a dose of 50 mg (S)-ketamine lies at 50 to 200 ng/mL, or wherein the maximum plasma concentration of (S)-ketamine following administration of a dose of 100 mg (S)-ketamine lies at 100 to 200 ng/mL.

14. The oral thin film according to claim 1, wherein the maximum plasma concentration of the ketamine metabolite (S)-norketamine following administration of a dose of 50 mg (S)-ketamine lies at 200 to 400 ng/mL, or wherein the maximum plasma concentration of the ketamine metabolite (S)-norketamine following administration of a dose of 100 mg (S)-ketamine lies at 300 to 500 ng/mL.

15. The oral thin film according to claim 1, wherein the maximum plasma concentration of the ketamine metabolite (S)-hydroxynorketamine following administration of a dose of 50 mg (S)-ketamine lies at 50 to 150 ng/mL, or wherein the maximum plasma concentration of the ketamine metabolite (S)-hydroxynorketamine following administration of a dose of 100 mg (S)-ketamine lies at 100 to 250 ng/mL.

* * * * *